US012558363B2

(12) United States Patent
Grases Freixedas et al.

(10) Patent No.: US 12,558,363 B2
(45) Date of Patent: Feb. 24, 2026

(54) COMPOSITIONS FOR CLINICAL COMPLICATIONS ASSOCIATED TO DEVICES IMPLANTED IN THE URINARY TRACT

(71) Applicants: Devicare SL, Cerdanyola del Vallès (ES); Universidad De Les Illes Balears, Palma de Mallorca (ES)

(72) Inventors: Felix Grases Freixedas, Palma de Mallorca (ES); Jordi Cuñe Castellana, Cerdanyola del Vallès (ES); Antonia Costa-Bauzá, Palma de Mallorca (ES); Paula Calvó García, Palma de Mallorca (ES); Sebastián Albertí Serrano, Palma de Mallorca (ES); Margalida Mateu Borrás, Palma de Mallorca (ES)

(73) Assignees: Devicare SL, Cerdanyola del Vallès (ES); Universidad De Les Illes Balears, Palma de Mallorca (ES)

( * ) Notice: Subject to any disclaimer, the term of this patent is extended or adjusted under 35 U.S.C. 154(b) by 848 days.

(21) Appl. No.: 17/790,359

(22) PCT Filed: Dec. 29, 2020

(86) PCT No.: PCT/EP2020/087955

§ 371 (c)(1),
(2) Date: Jun. 30, 2022

(87) PCT Pub. No.: WO2021/136765

PCT Pub. Date: Jul. 8, 2021

(65) Prior Publication Data

US 2023/0093480 A1 Mar. 23, 2023

(30) Foreign Application Priority Data

Dec. 30, 2019 (EP) .................................... 19383215

(51) Int. Cl.

| | |
|---|---|
| ***A61K 31/6615*** | (2006.01) |
| ***A61K 31/197*** | (2006.01) |
| ***A61K 31/522*** | (2006.01) |
| ***A61L 29/08*** | (2006.01) |
| ***A61L 29/16*** | (2006.01) |
| ***A61P 13/02*** | (2006.01) |
| ***A61P 31/04*** | (2006.01) |

(52) U.S. Cl.

CPC ........ *A61K 31/6615* (2013.01); *A61K 31/197* (2013.01); *A61K 31/522* (2013.01); *A61L 29/08* (2013.01); *A61L 29/16* (2013.01); *A61P 13/02* (2018.01); *A61P 31/04* (2018.01); *A61L 2300/204* (2013.01); *A61L 2300/214* (2013.01); *A61L 2300/216* (2013.01); *A61L 2300/404* (2013.01)

(58) Field of Classification Search

None

See application file for complete search history.

(56) References Cited

U.S. PATENT DOCUMENTS

| | | | |
|---|---|---|---|
| 2019/0091375 A1* | 3/2019 | Taton .................... | A61L 29/148 |
| 2019/0106032 A1* | 4/2019 | Lindhorst ............ | B60N 2/5858 |
| 2019/0216873 A1 | 7/2019 | Grases Freixedas et al. | |

FOREIGN PATENT DOCUMENTS

| | | |
|---|---|---|
| GB | 2533975 A | 7/2016 |
| WO | WO-2021136765 A1 | 7/2021 |

OTHER PUBLICATIONS

Siener et al. (Effect of L-Methionine on the Risk of Phosphate Stone Formation, Endourology and Stones, Urology 98, 2016). (Year: 2016).*

Stickler et al. (The encrustation and blockage of long term indwelling bladder catheters: a way forward in prevention and control, Spinal Cord 48, 784-790 (2010). (Year: 2010).*

Devicare, "Devicare gets the patent for its sensor technology in Europe and USA," Devicare.com, accessed at URL:[https://www.devicare.com/en/devicare-obtiene-la-patente-en-europa-y-estados-unidos-de-su-tecnologia-sensorica/] on Aug. 23, 2022, 1 page (Sep. 6, 2018).

International Search Report and Written Opinion for International Application No. PCT/EP2020/087955, European Patent Office, Netherlands, mailed on Apr. 13, 2021, 10 pages.

* cited by examiner

*Primary Examiner* — Melissa S Mercier

(74) *Attorney, Agent, or Firm* — STERNE, KESSLER, GOLDSTEIN & FOX P.L.L.C.; Jaume M. Canaves

(57) ABSTRACT

It is provided a composition comprising phytic acid or a pharmaceutically acceptable salt thereof, for use in reducing or preventing microorganisms' proliferation and/or encrustations caused by a urinary tract device implanted in a subject, thereby preventing or treating clinical complications related to microorganisms' proliferation and/or encrustations. The composition can further comprise a urine acidifier such as methionine, a crystallization inhibitor such as theobromine and/or other agents.

20 Claims, 6 Drawing Sheets

A

B

A

B

C

COMPOSITIONS FOR CLINICAL COMPLICATIONS ASSOCIATED TO DEVICES IMPLANTED IN THE URINARY TRACT

CROSS-REFERENCE TO RELATED APPLICATIONS

The present patent application is a 35 U.S.C. § 371 National Phase Application of International Application No. PCT/EP2020/087955, filed Dec. 29, 2020, which claims the priority benefit of European Application No. EP19383215.1, filed Dec. 30, 2019, both of which are herein incorporated by reference in their entireties.

FIELD OF THE INVENTION

The present invention relates to the field of medicine and particularly to compositions and methods to reduce micro-organisms' proliferation, encrustations and complications thereof, caused by a urinary tract device implantation such as a Foley's catheter.

BACKGROUND ART

Chronic diseases caused 36M deaths in 2008 worldwide and represent the main expense of the National Health Systems, according to the WHO. The monitoring of these diseases from the patient's home is one of the main challenges of 21st Century due to the social and economic impact that this entails for the Society.

In many chronic conditions, urinary incontinence or bladder control and drainage are present and aging is a factor in many of them, therefore, population ageing is increasing the incidence of these chronic problems. One third of the men and women between the age of 30- and 70-years face loss of bladder control at some point in their adult life. As a result, health authorities are seeking to lessen the burden by using technology to support a move towards self-care and outpatient long-term monitoring. Management of this type of urinary problems in many patients requires long-term implantation of an indwelling catheter. Prevalence studies report that 12-21% of patients in acute hospitals and 6-13% in the community have a urinary catheter. A long-term catheter is generally used because of a serious illness or disability.

There is no closed and standardized definition or time-frame to consider a patient as long term catheterized but is widely accepted a period of at least 30 days. Long term indwelling urinary catheters (LTIC) are the number one cause of infection in healthcare. The European point prevalence survey 2016 conducted by the European Centre for Disease Prevention and Control (ECDC) revealed that healthcare-associated urinary tract infection (UTI) accounted for 25.2% of all healthcare associated infections, followed by pneumonia/lower respiratory tract infection (LRTI) (24.4%) and surgical site infections (15.4%). In urology clinics, nearly 10% of hospitalized patients develop UTIs, often due to multi-drug resistant uropathogens. Among hospital-acquired UTIs, about 75% are associated with a urinary catheter, which is received by between 15-25% of hospitalized patients. Also, AMR (antimicrobial resistance) is responsible for an estimated 25,000 deaths per year in the EU. It is also estimated that AMR costs the EU EUR 1.5 billion per year in healthcare costs and productivity losses.

In Table 1 are disclosed the most relevant groups of patients affected by LTIC together with the prevalence of morbidities and complications associated to catheter indwelling.

TABLE 1

Most relevant groups of patients affected by LTIC and % of patients with the most relevant complication of each group.

| Patient using a LTIC | Prevalence in $10^3$ people |
|---|---|
| Patients with neurological conditions which cause bladder dysfunction (retention) | ≈162 |
| Patients lacking cognitive function (dementia) | ≈106 |
| Paralyzed, comatose or terminally ill patients (spinal cord injury) | ≈60 |
| Other reason (multiple sclerosis, diabetes) | ≈122 |

| Problems reported at least once per person 1 year (sample - 202 patients) | Percentage (%) |
|---|---|
| CAUTI | 57 |
| Blockage | 34 |
| Accidental dislodgment | 28 |
| Sediment | 87 |
| Bypassing | 67 |
| Bladder spasm | 59 |
| Kinks/twist | 42 |
| Catheter pain | 49 |

Catheter-Associated Urinary Tract Infections (CAUTIs) and associated encrustations and blockages are frequent key serious complications to catheter implantation. Sudden catheter blockage can be distressing. It can occur at any time and is a common emergency. Both CAUTIs and blockages have side effects and diminish the patient's quality of life as well as having an impact in the associated healthcare costs as well as in the indirect costs (such as cost of care and loss productivity). Only in the UK the problems resulting from the use of the Foley catheter costs the National Health Service between £1.0-2.5 billion and accounts for approximately 2,100 deaths per year. In the UK the permanent long-term catheter users are 3%, reaching 13% amongst care home residents and these figures are expected to rise because of the aging population. The prevalence of CAUTI for these patients is 57% while blockages are reported for 34% of users. Catheter removal may be the only management option for catheter blockage and recurrent infection. However, frequently changing an indwelling catheter may lead to increased risk of infection and further discomfort and embarrassment for the wearer. Thus, there is a strong rationale for a routine care strategy, which will help to prevent the development of catheter-associated complications and frequent removal.

The fundamental reason why catheterized patients are so vulnerable to infection is that the catheter undermines the defense systems that protect the normal bladder against infection. The regular mechanical filling and emptying of the normal bladder helps to ensure that any bacteria able to contaminate the urethra or bladder are washed out from the urinary tract. With the Foley catheter in place, on continuous drainage into a urine collection bag, the bladder does not fill and the retention balloon ensures that a sump of residual urine is maintained below the level of the drainage eye-holes at the catheter tip (10-100 ml). As urine then trickles through the catheter rather than flushing the urethra, the migration of bacteria from the contaminated skin insertion site through the urethra is not impeded. In the bladder, the bacterial cells invade the sump of urine, which is being replenished from the kidneys. In this continuous culture system, rapid bacterial multiplication results in the development of enormous bacterial populations, generally of around $10^8$ cells per mL of urine. The longer the catheter has been in situ, the more likely it is that bacteriuria will occur. Once a catheter has been in place for about 4 weeks, the urine will become highly contaminated in all patients. The risk of CAUTI increases from 3% in the regular population to 10% per day of catheterization, reaching 100% after 30 days. Similarly, the risk of blockages in LTIC patients ranges from 40-50%. Initially, single species colonize the urine but, with time, more complex mixed communities composed of four or five species commonly develop in the urine. Antibiotics are not generally given to patients under these conditions, so contaminated urine can be flowing through a catheter throughout its scheduled life span, which can be up to 12 weeks. Bacteria stick to the catheter surface and, bathed in a trickle of warm urine, they flourish and biofilms develop.

In patients undergoing short-term catheterization (up to 7 days), 10-20% will develop bacteriuria. Biofilms will form on the catheter but are sparse and patchy in nature and, as the catheter only remains in place for a short period, are of little concern. In catheters being used for the long term management of patients disabled by strokes, spinal injury or neuropathies such as multiple sclerosis or motor neuron disease and those suffering from urinary incontinence or retention however, the biofilms become extensive and can have a profound effect on health and well-being. The most troublesome are the crystalline biofilms that encrust and obstruct the catheter lumen. These can develop rapidly and block the flow of urine. Consequently, urine either leaks around the outside of the catheter and the patient becomes incontinent or alternatively urine is retained causing painful bladder distension. If the blockage is not noticed and the catheter changed, reflux of urine to the kidneys occurs and serious complications such as pyelonephritis and septicemia can result.

All available catheter types are vulnerable to encrustation and currently, apart from changing the catheter, no effective methods are available for its prevention or control. The encrustations on catheters are usually composed of struvite and apatite. Struvite (magnesium ammonium phosphate) forms large, often coffin shaped crystals and apatite (a hydroxylated form of calcium phosphate in which some of the phosphate ions are replaced by carbonate) appears as microcrystalline aggregations. Scanning electron microscopy has revealed that large numbers of bacilli are associated with the crystalline formations.

Mixed populations of bacteria are commonly present and invariably contain species capable of producing the enzyme urease. When urease-producing bacteria highly common in CAUTIs are present, particularly *Proteus mirabilis, Proteus vulgaris*, and *Providencia rettgeri*, they colonize the catheter forming an extensive biofilm and, in addition, generate ammonia from urea, thus elevating the pH of urine. As the pH rises, crystals of calcium and magnesium phosphates precipitate in the urine and in the catheter surface. The continued development of this incrustations and encrustations (inside the channel or on the surface of the catheter respectively) difficult the urine flow and may lead to complete blockage impeding urine expulsion. High pH is also associated to higher risk for CAUTI. Urease is the driving force of the crystallization process. It hydrolyses urea in the residual bladder urine to produce two molecules of ammonia to every molecule of carbon dioxide causing a rise in pH. As the urine becomes alkaline, crystallization of the magnesium and calcium phosphates is induced. In the meantime, the bacteria colonize the catheter surfaces forming bacterial biofilm. Aggregation of the crystalline material occurs in the urine, on the catheter and in the developing catheter bacterial biofilm. This process continues until the accumulating crystalline deposits block the flow of urine through the catheter. There can be serious consequences for patients, particularly for those in community care where professional help is not immediately available.

Several species that colonize the urine of catheterized patients produce urease. These include *Pseudomonas aeruginosa, Klebsiella pneumoniae, Morganella morganii, Proteus* species, some *Providencia* species, *Staphylococcus aureus* and coagulase-negative staphylococci. Of these, *Proteus mirabilis* is most commonly associated with catheter encrustation and blockage. The urease of *P. mirabilis* is a particularly active enzyme, being able to hydrolyze urea several times faster than those produced by the other species. The results of experimental studies in laboratory models of the catheterized bladder demonstrated that the only species capable of raising the urinary pH sufficiently to cause extensive encrustation were *P. mirabilis, P. vulgaris* and *Providencia rettgeri*. The latter two organisms are only found in about 8% of catheter biofilms. During a prospective study of the urinary flora of patients undergoing long-term catheterization, it was observed that the acquisition of *P. mirabilis* induced a rapid rise in the urinary pH and resulted in frequent and recurrent catheter blockages.

Current strategies to prevent CAUTIs can be divided in three main categories. The first strategy is catheter care bundle, which includes catheter insertion and catheter maintenance policies directed towards minimizing the contamination and so infection and encrustation risks. The main drawback is the need of strict and clear protocols as well as trained staff.

In addition, OptiFlo® (IS Pharmaceuticals Ltd/BardCare) and Uro-Tainer® (B. Braun Ltd.) are citric acid monohydrate compositions intended for dissolving encrustations through routine catheter washouts. Nevertheless, there is a lack of consistent evidence for their efficacy. Moreover, catheter cleaning requires high degree of dexterity that extremely complicates patient care.

UroShield® (NanoVibronix™) is a small external medical device that can be attached to any indwelling urinary catheter designed to reduce biofilm. This is accomplished by generating and propagating low frequency low intensity ultrasonic energy throughout the catheter. However, no significant change was observed between treated and untreated catheters, suggesting that this system alone does not disperse the biofilm and needs to combine with antibiotics to show some efficacy.

In second place there is catheter modification based on antimicrobial coatings, but results until now are not as promising as expected. More sophisticated alternatives such as photo-initiated polymer biomaterials integrated into urinary catheters to minimize the formation of biofilms and reduce or eliminate the probability of infections induced by the use of standard catheters have also been proposed. Limitations of current CAUTIs prevention alternatives are reflected in the extensive number of research still being conducted in the field. All of the strategies are focused on better biomaterials, coatings, and limiting bacterial adhesion.

In third place, oral antimicrobial agents can be used in order to prevent CAUTIs, but two major drawbacks are associated: i) bacteria resistance phenomena and ii) limited effect over bacteria population which are often embedded in organic matrix like biofilm on the surface of the catheter.

Furthermore, diagnosis of symptomatic CAUTI can be difficult since it cannot be relied on a positive culture result or dipstick as these are usually positive in most patients with a urinary catheter after a few days of insertion. Diagnosing CAUTI is based on clinical assessment as most patients are elderly and may not able to communicate properly. A thorough examination of the patient is required; ruling out other sources of infection is essential before a diagnosis of CAUTI is made. As a guide, most patients with CAUTI may have bladder spasm, suprapubic tenderness, fever (>37.5-38.3° C.), and/or renal angle tenderness. Renal angle tenderness in the absence of any other underlying pathology suggests pyelonephritis. Since diagnosis of CAUTIs is difficult, preventive strategies are very necessary.

In spite of the efforts in the field, treating clinical complications caused by the implantation of a urinary tract device is still a major health problem and there is no effective prevention protocol. Thus, it would be desirable to provide new improved approaches for solving the problem.

SUMMARY OF THE INVENTION

One problem to be solved by the present invention may be seen as related to the treatment and prevention of urinary tract infections, encrustations and other complications, particularly CAUTIs, caused by the implantation of a urinary tract device as e.g. a Foley's catheter.

As discussed in the working examples herein, the inventors have identified that phytic acid or a pharmaceutically acceptable salt thereof reduces or prevents microorganisms' proliferation and at the same time reduces or prevents encrustations caused by the implantation of a urinary tract device, which are considered the driving forces that cause the clinical complications associated. The present inventors believe that no prior art document directly and unambiguously describes the use of phytic acid or a pharmaceutically acceptable salt thereof for reducing or preventing microorganisms' proliferation and/or encrustations caused by the implantation of a urinary tract device in a subject.

Without being bound to the theory, it is believed that this is the first time that it is provided a composition with the benefits described above. As mentioned above, the common strategies used in the art are far from solving the problem. It is believed that the present invention solves a technical problem which the skilled in the art have been attempting to solve for a long time and fulfills a long-felt need.

It is also believed that this is the first time that a composition shows beneficial effects in the context of a urinary tract device such as a Foley catheter. It is noted that the circumstances and biological processes when a device is implanted in the urinary tract device are very different to a urinary tract infection or a lithiasis without presence of an implanted device. The presence of a device implanted in the urinary tract of a patient triggers the formation of bacterial and crystalline biofilms on the surfaces and inside the device, which makes the situation much more complicated and with a faster progress than without presence of the device. The implanted device can be considered a nucleation point for the formation of encrustations. Thus, it is surprising for the inventors that the composition of the invention reduces encrustations mostly present in devices such as catheters (e.g. struvite) and at the same time reduces microorganisms' proliferation. With the compositions of the invention the bacteria-crystal association is preventing from taking place from the very beginning.

Thus, the herein discussed novel use of a composition phytic acid may be seen as a contribution to the art that changes the behavior of the skilled person; for instance, based on the teaching herein, it is plausible that e.g. a food supplement comprising the composition of the invention would be administered previous to the implantation of a urinary device or/and while having the device implanted in order to reduce or prevent microorganisms' proliferation and encrustations, thereby avoiding the potential clinical complications. This represents a great benefit especially for patients with a long-term catheterization.

In EXAMPLE 2, the inventors obtained the first evidence that the presence of phytate reduces the number of struvite crystals adhered to catheters, reducing struvite crystals encrustations, which represent one of the the most frequent crystals produced in the scenario of an implanted urinary tract device.

EXAMPLE 3 provides evidence that the presence of phytate reduces the number of bacteria adhered to a catheter, reducing in consequence the risk of bacteriuria and associated risk of urinary tract infection.

All together, the results show that the two driving forces of the complications associated to the implantation of a urinary tract device are addressed with the composition of the invention. Thus, the clinical problem is treated since the very beginning, i.e. the implantation of the device. As said before it is very important to manage this problem at a very early stage because e.g. the risk of developing CAUTI increases from 3% in the regular population to 10% per day of catheterization, reaching 100% after 30 days.

Unexpectedly, the composition of the invention has been found to be particularly effective in preventing or reducing struvite encrustation on urinary tract devices (e.g., Foley catheter). In particular, the composition of the invention has been found to be particularly effective to prevent and/or reduce struvite encrustation developed in the presence of infection by urea-splitting organisms. Accordingly, the compositions of the invention can be applied wherein the encrustation comprises struvite deposits in the presence of a urinary tract infection, e.g., a bacterial infection that hydrolyzes urea to ammonium.

Accordingly, a first aspect of the invention relates to a composition comprising phytic acid or a pharmaceutically acceptable salt thereof, for use in reducing or preventing microorganisms' proliferation in the urinary tract and/or encrustations on a urinary tract device, caused by a urinary tract device implanted in a subject, thereby preventing or treating clinical complications related to microorganisms' proliferation and/or encrustations.

The term "encrustation" as used herein refers to the formation of deposits, e.g., deposits of crystalline material, on a device inserted or in contact with the urinary tract of a subject, e.g., a urinary catheter or stent such as a Foley's catheter. The term encrustation refers both to the process of deposition on the device and to the deposit accumulated on the device (i.e., encrusted material, encrusted deposit). In some aspects, the terms encrustation and calcification are used interchangeably, although the term calcification refers mainly to presence of crystals with calcium.

The term "microorganisms' proliferation" is understood in this description as a synonym of microorganisms' growth, multiplication or colonization. Growth of microorganisms can be sessile (attached to a surface forming a biofilm, e.g. in this context attached to the surface of a device) or planktonic (growth in liquid state, in this context e.g. in urine).

As used herein, the term "urinary tract device" refers to any device that is inserted or in contact with the urinary tract of a subject and which is susceptible to bacterial colonization/encrustation. The term urinary tract device can denote, e.g., catheters or stents and are mainly used in case of urine retention or bladder dysfunction. "Device" and "medical device" are understood as synonymous and are used interchangeably in this description. "Urinary tract device" is understood in this description as a synonym of "urological device", i.e. related to the urinary tract and urogenital (or genitourinary) system.

The term "implantation" refers to the introduction or insertion of a device in the urinary tract. It is understood that the invention does not include the step of implanting the urinary device in the subject, thus the invention is not related to a method performed on the animal or human body.

The term "clinical complication" as used herein refers to a medical problem that occurs during the course of a disease or after a procedure or treatment. The complication may be due to a disease, procedure or treatment, or it may not be related to them. In the present disclosure, a complication is derived from the procedure of implantation of a urinary tract device, i.e. is derived from the infection and/or encrustation of the implanted device. An example of complication is CAUTI. Also, as used herein, a complication includes a medical problem, a symptom or a discomforting situation for the patient.

In another aspect, it is provided a composition comprising phytic acid or a pharmaceutically acceptable salt thereof, for use in the treatment or prevention of clinical complications derived from the implantation of a urinary tract device.

As described above, catheter-associated urinary tract infections (CAUTIs) and associated encrustations and blockages are frequent key serious clinical complications to catheter implantation. Thus, in another aspect the invention provides a composition as described above for use in the treatment or prevention of CAUTIs.

DETAILED DESCRIPTION OF THE INVENTION

Figure 1:
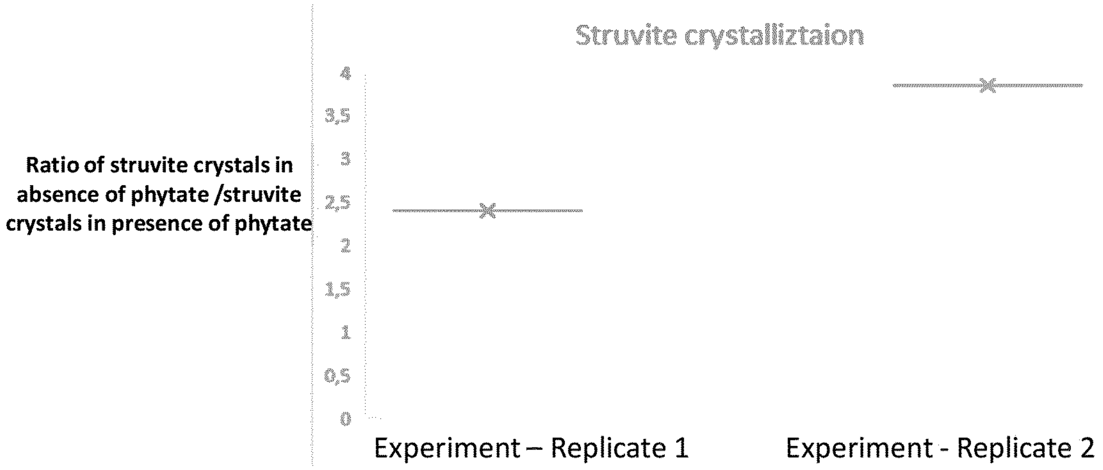
FIG. 1. Struvite crystals formation in presence or absence of phytate. It shows the ratios of reduction of struvite crystals formation in two different experiments (replicates) at 24 hours of reaction, where ratio is expressed as the number of struvite crystals without phytate divided by the number of struvite crystals with phytate.

Reducing or Preventing Microorganisms' Proliferation and/or Encrustations Caused by a Urinary Tract Device Implanted in a Subject. Thereby Preventing or Treating Clinical Complications Thereof As mentioned above, the first aspect of the invention relates to a composition comprising phytic acid or a pharmaceutically acceptable salt thereof, for use in reducing or preventing microorganisms' proliferation and/or encrustations caused by a urinary tract device implanted in a subject, thereby preventing or treating clinical complications related to microorganisms' proliferation and/or encrustations. Alternatively, this aspect can be formulated as the use of the composition of the invention for the manufacture of a medicament for reducing or preventing microorganisms' proliferation and/or encrustations caused by a urinary tract device implanted in a subject, thereby preventing or treating clinical complications related to microorganisms' proliferation and/or encrustations. Also, alternatively, the invention provides a method for reducing or preventing microorganisms' proliferation and/or encrustations caused by a urinary tract device implanted in a subject (particularly a human), thereby preventing or treating clinical complications related to microorganisms' proliferation and/or encrustations, comprising administering to said subject in need thereof the defined composition.

As discussed above, the implantation of a urinary tract device is the origin (i.e. the starting point) of frequent and serious clinical complications. When the device is implanted, the natural mechanical filling and emptying of the normal bladder that helps to ensure that any bacteria are washed out from the urinary tract, is disrupted. Thus, the migration of bacteria from the contaminated skin insertion site through the urethra is not impeded. In the bladder, the bacterial cells invade the sump of urine, which is being replenished from the kidneys. In this continuous culture system, rapid bacterial proliferation results in the development of enormous bacterial populations (bacteriuria). Thus, the first phenomenon and driving force is microorganisms' proliferation caused by the introduction of the device.

In this sense, in a particular embodiment, the composition comprising phytic acid or a pharmaceutically acceptable salt thereof is used in reducing or preventing microorganisms' proliferation caused by a urinary tract device implanted in a subject, thereby preventing or treating clinical complications related to microorganisms' proliferation. In another embodiment, the composition reduces microorganisms' proliferation in the urinary tract by at least reducing the adhesion of the microorganisms to the surface of the implanted device; said in other words, reducing sessile proliferation of the microorganisms. In another embodiment, the composition reduces sessile and planktonic proliferation of microorganisms' proliferation in the urinary tract.

When urease-producing bacteria are present—which is the most common situation—, they colonize the device forming an extensive biofilm and, in addition, generate ammonia from urea, thus elevating the pH of urine. Crystals of e.g. calcium and magnesium phosphate precipitate in the urine and in the device surface, generating encrustations. Since the pH rises, microorganisms' proliferation is further promoted and the situation becomes more complicated. pH increase in turn causes the precipitation of other crystals. Crystals bind to bacteria and precipitate on the device surfaces, or bacteria adhered to the device create several nucleation points for the generation of more encrustations.

Thus, in a particular embodiment, the composition reduces microorganisms' proliferation in the urinary tract by at least reducing the adhesion of the microorganisms to the surface of the implanted device, and wherein the composition further reduces or prevents encrustations on the surface of the device.

In a particular embodiment, the composition reduces encrustations or reduces microorganisms' proliferation by at least 2-fold, at least 4-fold, at least 6-fold, at least 8-fold, at least 10-fold, at least 12-fold, at least 14-fold, at least 16-fold or at least 18-fold compared to the encrustation/proliferation observed in control subjects. As observed in EXAMPLE 3, in a particular embodiment, the composition reduces microorganisms' proliferation (expressed as bacterial adhesion) by 18-fold. As observed in EXAMPLE 2, in a particular embodiment, the composition reduces encrustation by 4-fold.

In another embodiment, the composition prevents urine pH alkalinization.

In a particular embodiment the composition is used in the prevention clinical complications. As used herein, the terms "prevent," "preventing," and grammatical variants thereof refers, e.g., to partially or completely inhibiting encrustations/microorganisms' proliferation; delaying the onset of encrustations/microorganisms' proliferation; reducing the amount of encrustations/proliferated microorganisms; or reducing the rate of encrustations/microorganisms' proliferation. With respect to other effects resulting from the practice of the methods of the present invention, prevent refers, e.g., also to partially or completely inhibiting, delaying the onset, reducing the severity, reducing the rate, or reducing the amount of an undesired effect (e.g., pain or tissue damage caused by removal of the urinary device).

In some embodiments, the composition of the invention reduces:

(a) the risk or probability of encrustations/microorganisms' proliferation and of complications;

(b) the overall or total rate of encrustations/microorganisms' proliferation and of complications;

(d) the rate of encrustations/microorganisms' proliferation at the kidney end of the urinary tract device;

(e) the rate of encrustations/microorganisms' proliferation at the bladder end of the urinary tract device;

(f) the overall or total amount of encrustations/microorganisms' proliferation;

(g) the amount of encrustations/microorganisms' proliferation at the kidney end of the urinary tract device;

(h) the amount of encrustations/microorganisms' proliferation at the bladder end of the urinary tract device;

(i) encrustations/microorganisms' proliferation on the external surface of the urinary tract device;

(j) encrustations/microorganisms' proliferation on the internal surface of the urinary tract device;

(k) overall obstruction or occlusion of the urinary tract device;

(l) obstruction or occlusion at the kidney end of the urinary tract device;

(m) obstruction or occlusion at the bladder end of a stent of the urinary tract device; or, (n) a combination thereof.

In a particular embodiment the implantation of the urinary tract device is long term. There is no closed and standardized definition or timeframe to consider a patient as long term catheterized but is widely accepted a period of at least 30 days. For a long-term implantation, the term "indwelling urinary catheter" or "long term indwelling urinary catheter" (LTIC) is also used. Thus, in a particular embodiment the patient has the implanted device for at least 30 days.

In another embodiment the implantation of the urinary tract device is short-term, e.g. normally 7 days but also up to 30 days. This is the case e.g. when the patient has acute urinary retention due to e.g. a surgical intervention; in postoperative bladder decompression following surgery or pelvic trauma; and to monitor urinary output in acutely ill patients.

Patients

The terms "subject," "patient," "individual," and "host," and variants thereof are used interchangeably herein and refer to any mammalian subject, including without limitation, humans, domestic animals (e.g., dogs, cats and the like), farm animals (e.g., cows, sheep, pigs, horses and the like), and laboratory animals (e.g., monkey, rats, mice, rabbits, guinea pigs and the like) for whom diagnosis, treatment, or therapy is desired, particularly humans. The methods described herein are applicable to both human therapy and veterinary applications.

In particular embodiments the patient with an implanted device is a hospitalized patient, a patient with bladder dysfunction such as a patient with a neurological condition which cause bladder dysfunction, or a patient with urinary incontinence such as a patient lacking cognitive function (e.g. dementia or neuropathies), a paralyzed, comatose or terminally patient (with e.g. spinal cord injury). In other embodiments, the patient is suffering from other illnesses such as multiple sclerosis, stroke or diabetes.

Complications

In particular embodiments, the clinical complication derived from microorganisms' proliferation and/or encrustations caused by a urinary tract device implanted in a subject is selected from the group consisting of: bacteriuria, urinary tract infection, urethritis, pyelonefritis, sepsis, urinary tract device blockage, hydrophrenosis, renal failure, bladder distension, patient discomfort, catheter pain, polyuria, nocturia, dysuria, anuria, irritation, and combinations thereof.

In a particular embodiment, the complication is bacteriuria, which is an abnormally high concentration of bacteria in the urine, which can be asymptomatic (not involving infection) or symptomatic (when manifested as an infection). Usually, the process is that bacteriuria is a pre-infection step caused by the same implanted device that does not allow urine (and bacteria) to be removed. As they grow, and are not eliminated, the balance bacteria growing/bacteria being eliminated are not balanced, and often they culminate in infection (cystitis).

From here, and due to e.g. associated morbidity or low mobility, the development of upper urinary tract infections is more likely. And if upper urinary tract infection is developed, the risk of sepsis is also high.

In a particular embodiment, the complication is a urinary tract infection, particularly a lower urinary tract infection (e.g. initially) or an upper urinary tract infection. The lower urinary tract comprises urethra and bladder. Infection of urethra is also known as urethritis. The upper urinary tract comprises ureter and kidney. Infection of kidney is also known as pyelonephritis.

When the device inserted is a catheter, such as a Foley catheter, the urinary tract infection is known as CAUTI.

In a particular embodiment, the complication is septicemia or sepsis, usually named as urosepsis when sepsis is caused by a urinary tract infection.

In a particular, the complication is urinary tract device blockage, which occurs when the pathways for the removal of urine (different according to each device, e.g. the eyehole in case of a Foley catheter or a Doble J stent) are blocked by the growth of the biofilm and the crystalline biomass. This blockage, if partial, exacerbates bacteriuria (since less urine is removed and bacteria grow more) and if it is total, it involves change of the device and, if not done, severe complications such as sepsis or other complications.

In other embodiments, the composition of the invention is used to facilitate the removal of the device from the urinary tract, and to reduce tissue damage.

In a particular embodiment, the complication is hydrophrenosis, which is the swelling of a kidney due to a build-up of urine. It happens when urine cannot drain out from the kidney to the bladder mainly from a blockage or obstruction or by other causes such as urinary tract infection. Hydronephrosis can occur in one or both kidneys.

In a particular embodiment, the complication is renal ischemia, also known as nephric ischaemia, which is the deficiency of blood in one or both kidneys or nephrons, usually due to functional constriction or actual obstruction of a blood vessel.

In a particular embodiment, the complication is renal failure, due to a urinary tract infection or due to the pression increase (hydronephrosis) in the zone caused by device blockage.

In a particular embodiment, the complication is bladder distension.

In other embodiments, the complication is patient discomfort, catheter pain, polyuria (excessive or an abnormally large production or passage of urine), nocturia (need that a person has to wake up at night to go to urinate repeatedly), dysuria (painful urination), anuria (complete suppression of urination) or irritation (e.g. in the ureters). In a particular embodiment, the composition is useful to reduce pain and/or discomfort, or to improve quality of life of the patient.

If the flow of urine begins to decrease, the removal of urine is less effective and depending on the location of the blockage, there is flow through the outside part of the device and urine is not collected in the bag but spilled. Thus, in another embodiment the composition is useful for avoiding spilling of the urine outside the device and the collecting bag.

The composition of the invention is also useful in the prevention and treatment of symptoms such as e.g. bladder spasm, suprapubic tenderness, fever, renal angle tenderness (renal angle tenderness in the absence of any other underlying pathology suggests pyelonephritis).

Microorganisms' Proliferation

In a particular embodiment, the composition is used wherein microorganisms' proliferation and/or encrustations is caused by one or more microorganisms selected from the group consisting of *Pseudomonas aeruginosa, Klebsiella pneumoniae/oxytoca, Morganella morganii, Proteus* species (e.g. *P. mirabillis/vulgaris*), *Providencia* species (e.g. *Providencia rettgerilstuartii*), *Staphylococcus aureus, Escherichia coli, Serratia marcescens, Enterococcus* sp (e.g. *E. faecalis*), *Staphylococcus aureus, Enterobacter cloacae*, coagulase-negative staphylococci, and combinations thereof. These microorganisms are often present in the patient's own bowel flora.

In a more particular embodiment, microorganisms' proliferation and/or encrustations is caused by urease-producers microorganisms, such as *Proteus* species, *Klebsiella pneumoniae/oxytoca* and *Morganella morganii*. They colonize the device, e.g. a catheter, forming an extensive biofilm and, in addition, generate ammonia from urea, thus elevating the pH of urine.

More particularly the composition is used wherein microorganisms' proliferation is predominantly caused by *Proteus mirabilis, Proteus vulgaris* and *Providencia rettgeri* and more particularly, by *Proteus mirabilis*.

In another embodiment, the microorganisms' proliferation is caused by *Candida* sp, particularly by *Candida Albicans*.

A way to quantify the "reduction or prevention of microorganisms' proliferation" in the context of the implantation of a urinary device is, as shown in EXAMPLE 3, by quantifying the reduction of bacteria adhered to the device, i.e. the reduction in the bacteria biofilm formation, which can be considered one of the first steps driving the complications associated to the implantation of a device. In a particular embodiment, the composition of the invention reduces microorganisms' proliferation in the lumen/channel of the device. In another embodiment, the composition of the invention reduces microorganisms' proliferation on the outer surface of the device. In particular embodiments, the composition of the invention reduces microorganisms' proliferation (e.g. adhesion) predominantly present in the eyehole of the device, at the kidney end of the device, or over the surface of the entire device In another embodiment, the composition of the invention reduces microorganisms' proliferation (e.g. adhesion) inside and on the outer surface of the device.

In another embodiment, the composition of the invention reduces the amount of bacteria adhered to the device. In another embodiment, the composition of the invention reduces the rate of adhesion of bacteria to the device.

Encrustations

In a particular embodiment, encrustations comprise one or more crystals selected from the group consisting of ammonium phosphate crystals, calcium phosphate crystals, calcium oxalate crystals, uric acid crystals, and ammonium urate crystals.

"Crystals" can also be referred as "crystalline aggregations or formations" or "stones".

In a particular embodiment, encrustations comprise ammonium phosphate crystals, and more particularly of magnesium ammonium phosphate crystals (e.g. struvite). Struvite forms large, often coffin shaped crystals. Struvite is a magnesium ammonium phosphate crystal of formula $NH_4MgPO_4.6H_2O$. Struvite urinary crystals form readily in the urine of animals and humans that are infected with ammonia-producing organisms.

In some embodiments, encrustations comprise calcium phosphate crystals, and more particularly of brushite, or apatite crystals, particularly hydroxyapatite or carbaapatite (carbonated apatite). Brushita is a calcium phosphate crystal of formula $CaHPO_4.2H_2O$. Hydroxyaxapatite is a calcium phosphate crystal of formula $Ca_5(PO_4)_3(OH)$.

In some embodiments, depending on the patient conditions, the above-mentioned crystals (e.g. struvite, hydroxyapatite and brushite) can cause the generation of other crystals such as calcium oxalate crystals, particularly calcium oxalate monohydrate (COM) or dihydrate (COD) e.g. when high concentrations of calcium are present in urine.

In a particular embodiment, encrustations comprise ammonium urate crystals ($C_5H_7N_5O_3$). This crystal can be present in high concentrations of urate in urine and presence of ureolitic activity.

In a particular embodiment, encrustations comprise uric acid crystals, which appear e.g. when pH is low due to e.g. variations in urine pH due to the circadian rhythms.

In a particular embodiment, encrustations comprise cystine crystals, when a patient suffers from cystinuria, an inherited disease that is characterized by high concentrations of the amino acid cysteine in the urine.

In some embodiments, crystals comprise combinations (i.e. heterogeneous crystallization) of crystals mentioned above, since some crystals are nuclei for the precipitation of others.

In some embodiments, crystals are typically the ones found in CAUTIs, e.g. brushite (normally the first to precipitate), hydroxyapatite, and struvite.

The term "encrustation" in this description relates generally to presence of lithiasic crystals inside the urinary tract device and on the outer surface of the device. In particular embodiments, the composition of the invention reduces encrustations in the eyehole of the device causing the blockage of the urine. In another embodiment, the composition of the invention reduces encrustations on the outer surface of the device. In a particular embodiment, the composition of the invention reduces encrustations in the lumen/channel of the device (referred in the art as "incrustation"). In particular embodiments, the composition of the invention reduces encrustations predominantly present in the eyehole, at the kidney end of the device (renal part), or at the vesical part. In another embodiment, the composition of the invention reduces encrustations inside and on the outer surface of the device.

In another embodiment, the composition of the invention reduces the amount of encrustations. In another embodiment, the composition of the invention reduces the rate of encrustations.

In some embodiments, encrustations can be determined by visual examination or observation of the urinary tract device after extraction or in situ via endoscopy. In other aspects, encrustations can be measured for example using scanning electron microscopy, micro-analysis by dispersive energy of X rays, or by inductively coupled plasma atomic emission spectroscopy (ICP-AES). In some embodiments, the scale of encrustation can be determined according to a scale, e.g., 0 (without encrustation), 1 (sporadic calcifications/encrustations less than 1-2 $mm^2$), 2 (calcifications/encrustations of wide area greater than 1-2 $mm^2$), or 3 (complete blockage/obstruction/occlusion). In other embodiments, a 5 point score (0=none, 1=biofilm, 2=few crystals, 3=many crystals, 4=global calcification) scale can be used to quantify encrustations. In some embodiments, the risk of encrustations can be estimated or calculated by applying a blockage risk factor analysis or other methods known in the art.

Urinary Tract Device

Urologic devices, such as urinary catheter and stent types are vulnerable to encrustations and microorganism biofilm formation. In a particular embodiment, the urinary tract device is selected from the group consisting of: a urethral (Foley) catheter, a suprapubic (Foley) catheter, a ureteral stent (JJ stent), an intermittent catheter or Robinson catheter, a coudé catheter, a hematuria catheter, a condom catheter, a bladder balloon, a prostatic stent, a single J stent, a three-luer Foley, a nephrostomy device, an urostomy device, and an ostomy device.

In some embodiments, the urinary tract device is a urinary catheter. A urinary catheter is a latex, polyurethane, natural rubber or silicone tube inserted into the bladder through the urethra. Catheterization allows urine to drain from the bladder for collection. It may also be used to inject liquids used for treatment or diagnosis of bladder conditions. A catheter may be in place for long periods of time (indwelling catheter) or removed after each use. Types of urinary catheters are e.g. a urethral Foley catheter, an intermittent catheter/Robinson catheter, a coudé catheter, a hematuria catheter or a condom catheter.

In some embodiments, the urinary tract catheter is a urethral catheter (also named as Foley catheter or indwelling urinary catheter), which is retained by means of a balloon at the tip that is inflated with sterile water. A urethral Foley catheter has the purpose of draining and collecting urine from the bladder. It is a flexible tube that a clinician passes through the urethra and into the bladder to drain urine. It is the most common type of indwelling urinary catheter. The tube has two separated channels, or lumens, running down its length. One lumen, open at both ends, drains urine into a collection bag. The other has a valve on the outside end and connects to a balloon at the inside tip. The balloon is inflated with sterile water when it lies inside the bladder to stop it from slipping out. Manufacturers usually produce Foley catheters using silicone or coated natural latex. Coatings include polytetrafluoroethylene, hydrogel, or a silicon elastomer—the different properties of these surface coatings determine whether the catheter is suitable for 28-day or 3-month indwelling duration. The Foley catheter is connected to a retention balloon.

Urinary catheters are either inserted transurethrally or suprapubically. Suprapubic catheterization is usually used for bladder drainage following in bladder, urethral or pelvic surgery, or following genitourinary trauma. In practice, transurethral catheterization is the typical approach because the procedure can be organized and managed by nurses whereas suprapubic catheterization requires a more complex procedure.

Transurethral indwelling catheterization or urinary catheterization is defined as passage of a catheter into the urinary bladder via the urethra (urethral catheter). Transurethral indwelling catheterization is also called urethral catheterization. In some embodiments, the urinary tract device is a urethral indwelling (Foley) catheter.

Suprapubic catheterization is the insertion of a catheter into the bladder via the anterior abdominal wall. The catheter is inserted through an incision made above the pubic bone and below the umbilicus. The insertion of this type of catheterization is done by a urologic specialist. In some embodiments, the urinary tract device is a suprapubic catheter.

In a particular embodiment, the device is an intermittent catheter/Robinson catheter, which is a flexible catheter that is removed after each use. Unlike the Foley catheter, it has no balloon on its tip and therefore cannot stay in place unaided.

In a particular embodiment, the device is a coudé catheter, including Tiemann's catheter, designed with a curved tip that makes it easier to pass through the curvature of the prostatic urethra.

In a particular embodiment, the device is a hematuria catheter, which is a type of Foley catheter used for Post-TURP hemostasis. This is useful following endoscopic surgical procedures, or in the case of gross hematuria. There are both two-way and three-way hematuria catheters (double and triple lumen).

In a particular embodiment, the device is a condom catheter can be used by males and carries a lower risk of infection than an indwelling catheter.

In some embodiments, the urinary tract device is a bladder balloon. A bladder balloon is a small, lightweight device (about the size of a quarter) that floats within the urinary bladder. The balloon is designed to eliminate or reduce involuntary urinary leakage. It acts as a "cushion" to reduce the temporary pressure changes in the bladder that cause urinary leakage.

In some embodiments, the device is a stent. The term "stent" refers to a metal or plastic tube inserted into the lumen of an anatomic vessel or duct to keep the passageway open. "Ureteral stents" are a specific type of urinary tract device used to ensure the patency of a ureter, which may be compromised, for example, by a kidney stone. This method is sometimes used as a temporary measure to prevent damage to a blocked kidney until a procedure to remove the stone can be performed. JJ stents are a particular type of ureteral stent. "Prostatic stents" another specific type of "urinary tract device" placed from the bladder through the prostatic and penile urethra to allow drainage of the bladder through the penis. This is sometimes required in benign prostatic hypertrophy.

In some embodiments, the urinary tract device is a JJ stent. The terms "JJ stent", "double J stent," and "double pigtail stent" are used interchangeably and refer to a specially designed hollow tube, made of a flexible plastic material that is placed in the ureter and drains urine from the kidney to the bladder and it expect to stay in place temporarily or permanently. The ureter is the natural tube that transmits urine from the kidney to the bladder. The length of the stents used in adult patients varies between 24 to 30 cm. Because the stent coils like a J in the bladder and like an inverted J in the kidney, it is referred to as a JJ stent.

In a particular embodiment, the urinary tract device is a three-luer Foley catheter (used for irrigation, specially in hematuria cases). This catheter has three ways, one to inflate the balloon, one for passage of the urine and one for washing if necessary.

In some embodiments, the urinary tract device is a prostatic stent, which is a stent used to keep open the male urethra and allow the passing of urine in cases of prostatic obstruction and lower urinary tract symptoms (LUTS). Prostatic obstruction is a common condition with a variety of causes. Benign prostatic hyperplasia (BPH) is the most common cause.

In some embodiments, the urinary tract device is a nephrostomy device. A nephrostomy is an artificial opening created between the kidney and the skin which allows for the urinary diversion directly from the upper part of the urinary system (renal pelvis). The device used in this procedure is e.g. a single J stent. Nephrostomies are created by surgeons or interventional radiologists and typically consist of a catheter, which pierces the skin and rests in the urinary tract. Urine is collected in an external bag, which can be emptied as often as necessary.

In a particular embodiment, the urinary tract device is a urostomy device. A urostomy is a surgical procedure that creates a stoma (artificial opening) for the urinary system. A urostomy is made to avail for urinary diversion in cases where drainage of urine through the bladder and urethra is not possible, e.g. after extensive surgery or in case of obstruction.

In a particular embodiment, the urinary tract device is an ostomy pouching system, which is a prosthetic medical device that provides a means for the collection of waste from a surgically diverted biological system (colon, ileum, bladder) and the creation of a stoma. Pouching systems usually consist of a collection pouch plastic bag known as a one-piece system or, in some instances involves a mounting plate, commonly called a flange, wafer or a baseplate, and a collection pouch that is attached mechanically or with an adhesive in an airtight seal, known as a two-piece system.

Compositions of the Invention

As used herein, phytic acid (i.e. IP6) or its pharmaceutically acceptable salts refers also to other polyphosphorylated inositol compounds known in the art (e.g., IP2, IP3, IP4 or IP5). In a strict sense, the terms "phytate," "phytic acid," and "phytin," may be differentiated as follows: "phytate" refers to an anionic form of phytic acid; "phytic acid" refers to inositol hexaphosphate, a compound that occurs naturally in plants, including particularly plant leaves, and that may serve as a substrate for the enzyme phytase; and "phytin" refers to a salt of phytic acid, such as a calcium-magnesium salt of phytic acid. It is understood, accordingly, that "phytate," "phytic acid," and "phytin" are chemically related and interconvertible forms having a shared chemical structure. As used herein, therefore, "phytate," "phytic acid," and "phytin" are interchangeable terms in as much as they are highly related, similar, chemically interconvertible. Thus, where only one of the terms "phytate," "phytic acid," or "phytin" is used in the descriptions of the methods disclosed herein, it is understood to function as a representative term.

In particular embodiments, "phytic acid" or "myo-inositol-hexaphosphate," is understood as the molecule of the formula:

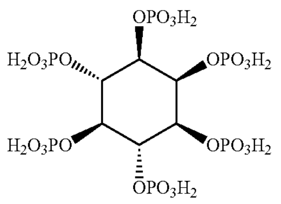

and "phytate" is the form of phytic acid with at least one less hydrogen, so that the corresponding phosphate group interact with a cation (e.g. K, Mg, Ca, Mn, Zn, or Fe).

In a particular embodiment, phytic acid and/or its pharmaceutically acceptable salts is used in free form as pure substances.

In particular embodiments, phytic acid and/or its pharmaceutically acceptable salts are derived from a portion of a plant species rich in phytic acid or its salts, or from a plant extract of said plant species, such as, for example, extracts of brown rice, or carried by plant species containing them, such as the germs or the external parts of wheat, oat, soy, almond, locust bean, etc. grains or fruits. In a particular embodiment, the plant extract is, e.g., a rice husk extract (also known as a rice bran extract) enriched in phytic acid magnesium and calcium salts.

In another more particular embodiment, the pharmaceutically acceptable salt of phytic acid is selected from sodium phytate, potassium phytate, calcium phytate, magnesium phytate or zinc phytate or calcium-magnesium phytate and combinations of the same. More particularly, the pharmaceutically acceptable salt of phytic acid is selected from calcium-magnesium phytate and sodium phytate or combinations of the same.

In a particular embodiment, the composition is administered in combination with at least one urinary acidifier.

The term urinary acidifier is referred to all those substances currently known which when supplied orally, decrease urinary pH values. In a particular embodiment the urinary acidifier is selected from a portion or an extract of the plant species *Vaccinum* sp. (particularly *Vaccinum macrocarpum*), pharmaceutically acceptable ammonium salts, arginine or any of its pharmaceutically acceptable salts, cysteine or any of its pharmaceutically acceptable salts, methionine or any of its pharmaceutically acceptable salts or mixtures thereof and more particularly the urinary acidifier is methionine.

In a particular embodiment, methionine is in form of extract. Sources of methionine are e.g. beef lean ground patty, eggs, fish (salmon), milk, refried beans, or almond.

In some embodiments, the composition comprises phytic acid or salts thereof in an amount between 10 mg and 10,000 mg per dose. Particularly, phytic acid or salts thereof is in an amount between 50 and 1,000 mg, particularly in an amount between 50 and 200 mg, and more particularly, in an amount around 50, 100, 150, or 200 mg. More particularly, phytic acid or salts thereof is in amount around 170 mg. In another embodiment, the composition comprises between 5-40% by weight of phytic acid or salts thereof and between 20-70% by weight of the urinary acidifier. In particular embodiments the composition comprises between 10-15% of phytic acid or salts thereof and around 60% of acidifier. Particularly, the acidifier such as methionine is in an amount between 50 and 10,000 mg, particularly in an amount between 50 and 1000 mg, and more particularly between 100 and 700 mg. More particularly, the acidifier is in amount around 50, 100, 150, 200, 250, 300, 350, 400, 450, 500, 550, 600, 650 or 700 mg.

In another embodiment, the composition is in a form suitable for oral, parenteral, enteral or intravenous administration.

Other Active Ingredients in Combination

In a particular embodiment, the composition is combined with theobromine, which acts as a molecular imposter becoming a crystallization inhibitor against uric acid crystals. Theobromine is particularly added to the composition when urine pH is low to prevent uric acid crystallization. However, it is important to prevent uric acid crystallization not only due to a possible excessive acidification caused by e.g. other agents of the composition, but also due to the circadian variation of pH (more acidic pH during the night), patient particularities, when diet is rich in proteins e.g., or the person has hyperuricosuria (high uric acid concentrations in the urine).

Theobromine ($C_7H_8N_4O_2$, chemical name 3,7-dimethylxanthine or 3,7-dihydro-3,7-dimethyl-1H-purine-2,6-dione) is an alkaloid from the methylxanthine family, a family that also includes theophylline and caffeine. In some embodiments, theobromine is used in pure form or as an extract from natural products. Theobromine e.g. is present in high amounts in cocoa and chocolate. Cocoa powder can vary in the amount of theobromine, from 2% theobromine, up to higher levels around 10%. There are usually higher concentrations in dark than in milk chocolate. A 50 g piece of black or bitter chocolate, which contains a minimum of 34% up to a maximum of 98% cocoa, may contain an average of 378 mg theobromine. Theobromine can also be found in small amounts in the kola nut (1.0-2.5%), the guarana berry, yerba mate (*Ilex paraguariensis*), and the tea plant. Cocoa beans naturally contain approximately 1% theobromine. The plant species with the largest amounts of theobromine are: *Theobroma cacao, Theobroma bicolor, Ilex paraguariensis, Ilex guayusa, Camellia sinensis, Cola acuminate, Theobroma angustifolium, Guarana, Coffee Arabica*. In particular embodiments, theobromine is used in form of extract of cocoa or chocolate, and more particularly a cocoa extract in powder form with 40% of flavonols (theobromine) is used.

In other embodiments, the composition further comprises an ingredient commonly used to treat or prevent urinary tract infections such as e.g. cranberry (*Vaccinium macrocarpon*) *salvia* (*Salvia officinalis*), D-mannose, vitamin C (ascorbic acid), probiotic bacteria, hibiscus, or Boswellia sacra.

In other embodiments, the composition further comprises crystallization inhibitors such as citric acid or salts thereof (particularly as potassium citrate or magnesium citrate). In some embodiments, the composition comprises magnesium. Magnesium may be supplied in the form of its pharmaceutically acceptable salts such as e.g. magnesium oxide, magnesium hydroxide, magnesium citrate, magnesium stearate, magnesium carbonate, magnesium chloride and magnesium sulfate or as an extract rich in magnesium. Extracts rich in magnesium are from e.g. almonds, spinach, cashews, peanuts, cereal, or black beans.

In other embodiments, the composition further comprises enzymes or probiotic bacteria expressing these enzymes (particularly oxalate decarboxylase) that catalyze the degradation of oxalate. Particular probiotic are lactic acid bacteria able to degrade oxalate. In other embodiments, probiotic bacteria are *Oxalobacter* sps, and more particularly *Oxalobacter formigenes*. The composition can also comprise antioxidants such as polyphenols, vegetal extracts or vitamin C.

In a particular embodiment, the composition comprises phytic acid or salts thereof, methionine and theobromine. In an embodiment, the composition comprises between 10-40% of theobromine and particularly 25%. In a particular embodiment, theobromine is in an amount between 50-400 mg as cocoa extract in powder form with 40% of theobromine. In a more particular embodiment, theobromine is in an amount between 50 and 200 mg, and more particularly, in an amount around 50, 100, 150 or 200 mg.

In other embodiments, the composition comprises calcium-magnesium phytate or sodium phytate, methionine, theobromine and ascorbic acid. In a particular embodiment, ascorbic acid is in an amount between 20-250 mg.

In an embodiment, the composition comprises at least one polyphenol. Polyphenols is a group of chemicals found in plants characterized by the presence of more than one phenol group per molecule. These products have significant antioxidant properties and are also suitable for human consumption. In some embodiments, polyphenols included in the composition are those extracted from the seeds of red grapes or white grapes, although they may come from other plant species such as berries, tea, beer, olive oil, chocolate/cocoa, nuts, pomegranates, etc. Specific examples of particular polyphenols are epicatechin, catechin, gallocatechin, epigallocatechin, quercetin, resveratrol, tannic acid or gallic acid.

In another embodiment, the composition is combined with a mucolytic agent. Mucolytic agents are defined as agents able to break down mucus or to reduce mucus viscosity. In the context of the invention, the mucolytic agent (e.g. N-Acetylcysteine, NAC) is able to reduce or prevent biofilm formation on a urinary tract device implanted in a subject, i.e. to reduce or prevent microorganisms' proliferation and/or encrustations caused by a urinary tract device implanted. This biofilm (also known in this field as "organic film" or "conditioning film") appears universally in all kinds of indwelling urological devices becoming a trigger for complications such as associated urinary infections. Thus, the conditioning film not only facilitates the formation and establishment of bacterial films, with the greater implicit resistance of these structures but also represents a point of crystalline heteronucleation resulting in the aforementioned virulence and resistance mechanisms on the part of bacteria.

The inventors have demonstrated that N-acetylcysteine in combination with phytate reduces the accumulated protein (as representative material of the conditioning film) on a medical device fragment in a system simulating a urinary tract (EXAMPLE 5).

In particular embodiments, the mucolytic agent can be any agent known in the art that makes the function of "breaking down mucus or reducing mucus viscosity". Some examples can be: drugs such as N-acetylcysteine, acetylcysteine, carbocysteine, ambroxol (trans-4-[(2-Amino-3,5-dibromobenzyl)amino]cyclohexanol), bromhexine, dornase alfa (purified solution of recombinant human deoxyribonuclease I), MeSNa (sodium 2-mercaptoethanesulfonate), or sobrerol (trans-p-Menth-6-ene-2,8-diol); molecules such as aescin or glycirrinic acid, essential oils like peppermint oil, or essential oils rich in phytochemicals with ketone and lactone groups in their chemical structure, such as verbenone, thujone, carvone, cryptone, pulegone, menthone, and pinocamphone; vegetals or vegetal extracts such as ivy leaf, cardamon, garlic, cayene pepper, *Echinacea purpurea, Sambucus nigra, Glycyrrhiza glabra, Vitex trifolia, Zingiber officinale*, rosemary (*Salvia rosmarinus*) and pine (*Pinus*).

In a particular embodiment, the mucolytic agent is N-acetylcysteine (NAC). In an embodiment, the composition comprises 5-80% of NAC, and particularly 20%. In a particular embodiment, NAC is in an amount between 100-3000 mg. In another particular embodiment, NAC is in an amount between 100-600 mg, particularly 200 mg, for example if NAC is added in a food, a food supplement or a medical food. In an embodiment, NAC is administered to the subject in a daily dose of 600 mg, for example in three doses of 200 mg.

In an embodiment, the composition comprises phytic acid or salts thereof and NAC. In a particular embodiment, the composition comprises phytic acid or salts thereof, NAC, methionine and theobromine. In an embodiment, the composition comprises between 5-40% of theobromine, between 20-70% of methionine, between 5-80% of NAC and 5-50% of phytic acid or salts thereof.

In another embodiment, the composition comprises 15% of phytic acid or salts thereof, 20% of NAC, 50% of methionine, and 15% of cocoa extract rich in theobromine (which represents 6% of theobromine). An example of product can be a dried powder composition comprising: 170 mg of rice husk extract rich in calcium-magnesium phytate, 500 mg of methionine, 150 mg of cocoa extract rich in theobromine and 200 mg of NAC.

In some embodiments, the compositions disclosed herein can be applied in combination with antibiotic therapy, e.g., co-administration with antibiotics known in the art generally used to treat urinary tract infections. In some embodiments, the antibiotic comprises penicillin (e.g., ampicillin, amoxicillin, mecillinam, or amoxicillin clavulanate), sulfonamide (e.g., trimethoprim-suldamethoxazone), cephalosporin (e.g., cefadroxil, cefazolin, cephalexin, cephradine, cefaclor, cefamandole, cefotetan, cefoxitin, cefuroxime, cefdinir, cefixime, cefoperazone, cefazidime, ceftriaxone, or cefepime), fluoroquinolone (e.g., ciprofloxacin, enoxacin, gatigloxacin, levofloxacin, norfloxacin, or ofloxacin), aminoglycoside (e.g., gentamicin), nitrofurantoin, forfomycin, or any combination thereof. In some embodiments, the antibiotic is administered before, after, or concurrently with the compositions disclosed herein. In some embodiments, antibiotics are applied before, during, or after, the implantation of a urinary tract medical device, in the urinary tract of a patient in need thereof.

The administration of the ingredients can be separately (waiting a time interval between the administration of e.g. phytic acid and the acidifier), sequentially (one after the other), concomitantly (simultaneously) or in admixture (together). In a particular embodiment, the administration is concomitantly or in admixture. When the administration is separately, sequentially, or concomitantly, the agents of the composition of the invention can be separately forming a kit.

Administration Forms

In a particular embodiment the composition is in form of a pharmaceutical product (i.e. a medicament), a food supplement, a functional food, a medical food or a food for special medical purposes The compositions of the invention can be in the form of a pharmaceutical product. The term "pharmaceutical product" is understood in its widely meaning in this description, including any composition that comprises a principle ingredient—in this case, phytic acid and e.g. optionally methionine—together with pharmaceutically acceptable excipients. The term "pharmaceutical product" is not limited to refer to medicaments.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts. In some embodiments, excipients are selected from: Vinyl acetate Copolymer—Stabilizer E1208, Microcrystalline cellulose—Bulking agent E460, Calcium sulfate dihydrate—Stabilizer E516, Magnesium stearate—Stabilizer E470Eb, Silicon dioxide—Anticacking agent E551, Hydroxypropylmethylcellulose—Stabilizer E464, Microcrystalline cellulose—Stabilizer E460, matodextrine—bulking agent, and Stearic acid-Stabilizer E570.

The pharmaceutical product can adopt different forms or names depending on the product approval route and also depending on the country. For instance, a medicament is a particular pharmaceutical product. A medical food is considered in this description as another particular pharmaceutical product. The terms "medical food", "functional food"

or "food for special medical purposes" are used in some countries to refer to a food specially formulated and intended for the dietary management of a disease that has distinctive nutritional needs that cannot be met by normal diet alone. They are defined in regulations such as the Food and Drug Administration's 1988 Orphan Drug Act Amendments in the United States, and the Commission Directive 1999/21/EC in Europe. Medical foods are distinct from the broader category of food supplements and from traditional foods that bear a health claim. Thus, in a particular embodiment, the composition of the invention is a medical food.

Often, compositions such as the one disclosed herein, are considered as food supplements. A food supplement, also known as dietary supplement or nutritional supplement is considered another particular pharmaceutical product. This is a preparation intended to supplement the diet and provide nutrients or beneficial ingredients that are not usually ingested in the normal diet or may not be consumed in sufficient quantities. Mostly, food supplements are considered as food products, but sometimes they are defined as drugs, natural health products, or nutraceutical products. In the sense of the present invention, food supplements also include nutraceuticals. Food supplements are usually sold "over the counter", i.e. without prescription. If the food supplement adopts the form of a pill or a capsule, it comprises excipients which are the same as the used in medicaments.

The composition of the invention may be administrated in solid form (including tablets, lozenges, pills, capsules, granules, powders, suspensions, sachets, sweets, bars) or in liquid form (such as solutions, suspensions, syrups or emulsions), usually in the form of a unit dose. In turn, they may be administered as such or after being subjected to operations such as sterilization, addition of preservatives, addition of stabilizers or addition of emulsifiers.

The composition of the invention can be administered as such, can be mixed with a suitable drinkable liquid, such as water, yoghurt, milk or fruit juice, or can be mixed with solid or liquid food.

The composition may be combined with one or more compounds, which facilitate absorption thereof through the route of administration selected. Thus, they can be administered with lactose, sucrose, talc, magnesium stearate, cellulose, calcium salts, gelatin, fatty acids, as well as with other similar substances.

The pharmaceutically acceptable adjuvants and vehicles that may be used in said compositions are the adjuvants and vehicles known by the persons skilled in the art and commonly used in the preparation of therapeutic compositions.

For the preparation of a medicament, the composition will be in a pharmaceutically acceptable or substantially pure form, that is, having a level of pharmaceutically acceptable purity excluding the normal pharmaceutical additives such as diluents and carriers, and including no material considered toxic at normal dosage levels. The purity levels for the active principle are particularly higher than 50%, more particularly higher than 70%, and still more particularly higher than 90%. In a particular embodiment, they are higher than 95% of compound of formula (I), or salts or solvates thereof.

The pharmaceutical compositions can be in any form that allows for the composition to be administered to a patient. It is not the objective of this description to provide details of the formulations, excipients, administration forms, doses, etc. that are commonly known by the skilled in the art.

In some embodiments, the composition of the invention is administered to the subject before, after, and/or during (concurrently with) the implantation of the urinary tract device. Then, after implantation of the device, subsequent doses of the composition can be administered in a daily regime.

In some embodiments, the compositions of the present invention are administered e.g. at least once a day, at least twice a day, at least three times a day, or at least four times a day, but can be administered more times a day at the discretion of the specialist and depending on the circumstances of the patient. In some embodiments, the compositions are administered e.g. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least about 13 weeks, at least about 14 weeks, at least about 15 weeks, or at least about 16 weeks, also at the discretion of the specialist and depending on the circumstances of the patient. In a particular embodiment, the treatment lasts for as long as the device remains implanted, e.g. six months or a year.

Finally, in other embodiments, the composition of the invention is in the form of coating of the urinary tract device, as a liquid solution to do device washouts or instillations, or as patches to administrate to the patient. In some embodiments, the coating comprises the compositions of the invention together with e.g. a resin or a polymer and the coating is applied to the device in a post-manufacturing step. In some embodiments, the patches are dressings applied to the skin that allow the compositions of the invention to pass through the skin and spread systemically.

Monitoring pH for Selecting the Composition to be Administered

As discussed before, alkaline pH is associated to higher risk for urinary tract infection and encrustations. Thus, an aspect of the invention contemplates that the administration of the compositions of the invention can be conducted dynamically in response to measured variations in urine pH (e.g., as measured with a pH meter or pH dipsticks). Thus, depending on the value of pH, a composition according to the invention is selected.

In a particular embodiment, the target is to maintain the pH between 5.5 and 6.2 to avoid microorganisms' proliferation and encrustations after the implantation of the urinary tract device, and the complications thereof. In a particular embodiment, the composition to be administered comprises phytic acid or salts thereof, urine acidifier such as methionine and theobromine. If e.g. pH falls below 5.5 where the uric acid crystallizes, the composition can comprise a greater amount of theobromine and a lower amount of acidifier or the patient can take one pill less per day. If pH falls above 6.2 where the calcium phosphate, ammonium phosphate or ammonium urate crystallizes the composition can comprise a greater amount of urine acidifier, lower amount of theobromine or take one pill more per day. In a particular embodiment, in case e.g. the patient has cystinuria or metabolic acidosis, the composition of the invention comprises a very low amount of urine acidifier or is not present in the composition.

Thus, in some embodiments, all the doses administered to the patient have the same composition (i.e., the same formulation) during the duration of the treatment. In other embodiments, the doses administered to the patient can vary during the duration of the treatment, depending on e.g. patient particularities, urine pH, and diet.

In some embodiments, urine pH is measured e.g. at least 1 time per day, at least 2 times per day, at least 3 times per day, at least 4 times per day, at least 5 times per day, or at least 6 times per day. In some embodiments, urine pH is measured in all micturitions for 24 hours. In some embodiments, urine pH is measured immediately before administration of a composition of the present invention. In some embodiments, urine pH is measured after the administration of a composition of the present invention, e.g., after at least about 30 minutes, at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least 16 hours, at least about 17 hours, at least about 18 hours, at least about 19 hours, at least about 20 hours, at least about 21 hours, at least about 22 hours, at least about 23 hours, or at least about 24 hours.

In a particular embodiment, to practice the methods disclosed herein, urine pH measurements are performed using a device (e.g., a portable device) with sufficient resolution (e.g., 0.1 pH units) in order to provide quick and reliable pH measurements across a pH range encompassing the predetermined threshold pH values and/or the desired pH range, for example, a Lit-Control pH Meter from the company Devicare, S. L. described, e.g., at www.devicare.com/en/devicare-obtiene-lapatente-en-europa-y-estados-unidos-de-su-tecnologia-sensorica/.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. Furthermore, the present invention covers all possible combinations of particular and preferred embodiments described herein. The following examples and drawings are provided herein for illustrative purposes, and without intending to be limiting to the present invention.

EXAMPLES

Example 1: Crystallographic Characterization of Foley Catheters in Patients with Cognitive Failure or Spine Cord Injury Foley, urethral and suprapubic catheters are an essential tool in the management of patients without voluntary control of urination. Its use allows a continuous evacuation of the urine accumulated in the bladder, which is collected by means of a collection bag. However, intrinsically, its use implies the neutralization of natural defense mechanisms against bacterial colonization of bladder urine. As a consequence, bacteriuria and CAUTIs are practically unavoidable in this type of patient, practically reaching a full incidence if the implantation time exceeds 30 days. As a final consequence, prior to or simultaneously with the infection, the phenomenon of encrustation appears: it is a complication that changes from minor tissue lesions during replacement or extraction, to life-threatening conditions such as septicemia, the result of total blockage of urinary flow.

Methodology

Twenty-two urinary Foley catheters were collected from patients with cognitive failure and spinal cord injury taking advantage of their replacement. In order to make a correct interpretation, after the extraction of the probes, these were washed with a 0.5% thymol saline solution, and they were completely dried for 12-18 hours at room temperature. To be sent to the analysis laboratory and in order to avoid possible contamination, the bladder and renal part of the catheter were processed separately.

Results

All of the studied catheters showed a first internal deposit of organic matter. 50% of them and on the layer of organic matter, crystals of struvite (magnesium ammonium phosphate) appeared, indicating infection by ureolytic bacteria, although the obstruction was not total. In an 4.5% of the probes, the deposition of organic matter and struvite crystals caused a complete blockage of the same. The deposits always presented greater magnitude in the distal part, close to the collection bag.

According to the analysis performed, the embedding is a prevalent phenomenon in patients with Foley urinary catheters. The nature of the crystals detected, closely linked with the presence of positive urease microorganisms, is consistent with the complications associated with bladder catheterization.

Example 2: Effect of Phytate on Struvite Crystals

Once the ideal conditions of the in vitro struvite crystal development medium on the surface of the catheters have been established, it was intended to observe if there is a significant decrease in number of struvite crystals in the presence of phytate.

Methodology

Artificial urine: The crystalline development was carried out in an artificial urine medium with the compositions shown in Table 2 and Table 3.

TABLE 2

| Composition for artificial urine with calcium Composition A (no phytate) | |
|---|---|
| Substance | Concentration (g/L) |
| $Na_2SO_4 \cdot 10H_2O$ | 11.02 |
| $MgSO_4 \cdot 7H_2O$ | 1.46 |
| $NH_4Cl$ | 9.28/18.56 |
| KCl | 12.13 |

TABLE 3

| Composition for artificial urine with phytate Composition B (with phytate) | |
|---|---|
| Substance | Concentration (g/L) |
| $NaH_2PO_4 \cdot 2H_2O$ | 2.65 |
| $Na_2HPO_4 \cdot 12H_2O$ | 12.41 |
| NaCl | 13.05 |
| Phytate | 2 ppm |

Struvite crystals are completely associated to an alkaline pH and urease activity. Actually, until urine pH (or pH of artificial solutions) do not reach values close to 7, struvite components (molecules and cations) are dissolved, thus nucleation and growth cannot take place. For this reason, experiments with acidic pH values are not necessary, and are not thermodynamically possible. In base of that, the solutions were adjusted to pH 7.2, mixed in a 1:1 ratio adding 20 ml from Composition A and 20 ml from composition B in 50 mL falcon tubes where a 1.5 cm catheter portion had previously been placed. The mixture stood 24 h at 37° C. Once the established time expired, the catheter portions were removed. Some catheter portions were water washed (R fraction) while the rest did not (NR fraction).

Struvite crystals count: The last step was counting the crystals adhered over the surface of the not washed (NR) catheter portions, as the ones belonging to the washed portions suffer from an important crystal loss due to the washing procedure.

Results

Table 4 shows the effect of phytate in struvite crystal formations at different time of reaction expressed as the ratio of reduction of struvite crystals formation, where the ratio is the number of struvite crystals without phytate divided by the number of struvite crystals with phytate. These results illustrate phytate has the capability to act as crystallization inhibitor of struvite in presence of a catheter. FIG. 1 shows the struvite crystals formation ratio for the experiments at time of reaction of 24 hours.

TABLE 4

Effect of phytate in struvite crystals formation

| | # struvite crystals without phytate | # struvite crystals with phytate (2 ppm) | Struvite crystals formation ratio | Time of reaction |
|---|---|---|---|---|
| Experiment 1 | 29 | 20 | 1.45 | 12 hours |
| Experiment 2 | 12 | 5 | 2.4 | 24 hours |
| Experiment 3 | 25 | 6.5 | 3.85 | 24 hours |

Figure 2:
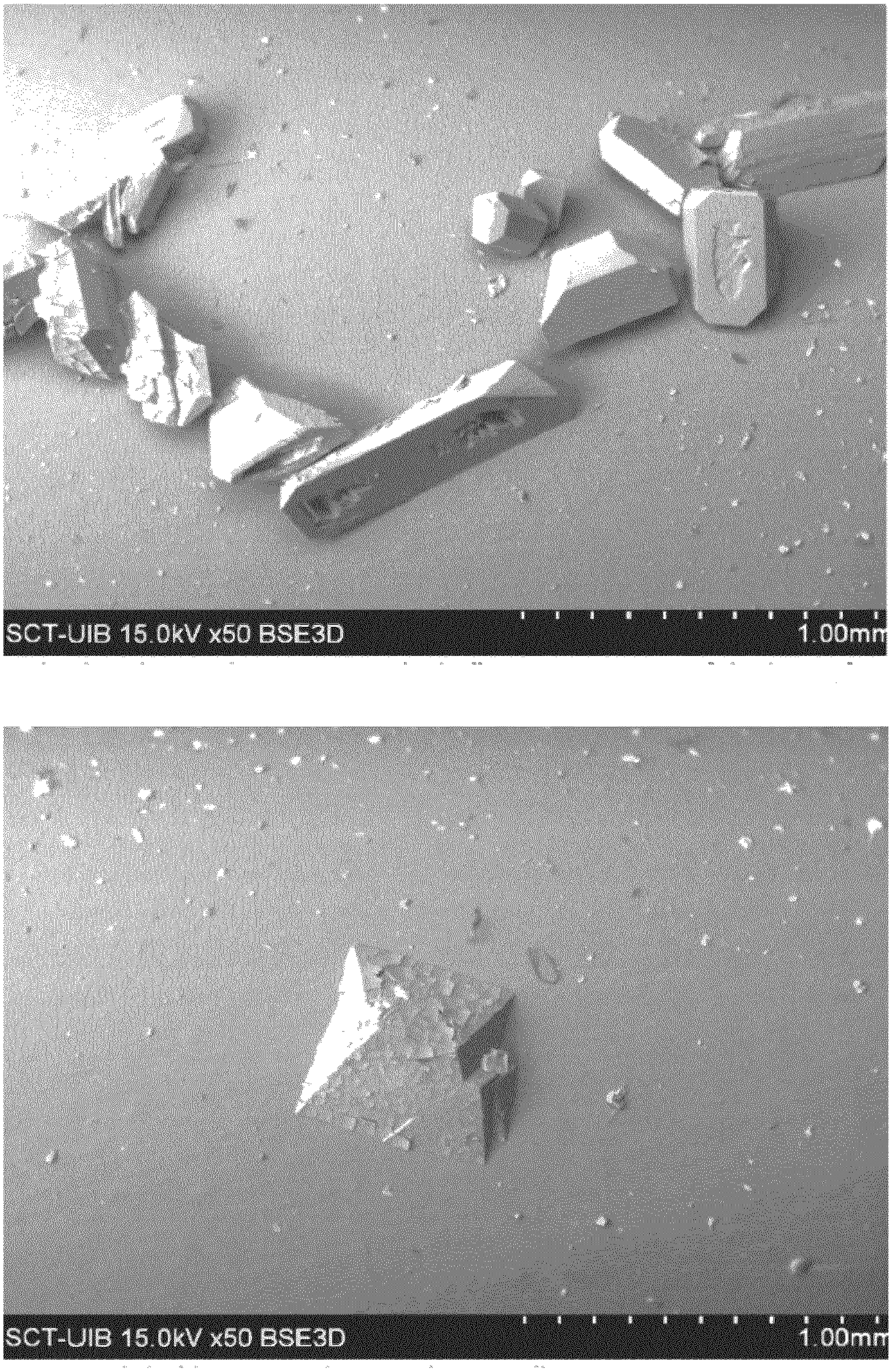
FIG. 2. Inhibition capability of phytate in struvite crystals formation. (A) shows electron microscopy image of struvite crystal formation without phytate, and (B) shows electron microscopy image of struvite crystal formation with phytate.

FIG. 2 show images taken with an electron microscope, being again illustrative of the phytate inhibition capability in struvite crystals formation in presence of a catheter. FIG. 2 A image was captured after 24 of reaction in a solution mimicking an infected urine. FIG. 2 B was obtained after 24 h or reaction with exactly the same solution but with 2 ppm of phytin (calcium magnesium phytate). As can be seen, crystals formed in presence of phytate present a window-shape and pyramidal morphology and are smaller than the crystals formed in absence of phytate.

Figure 3:
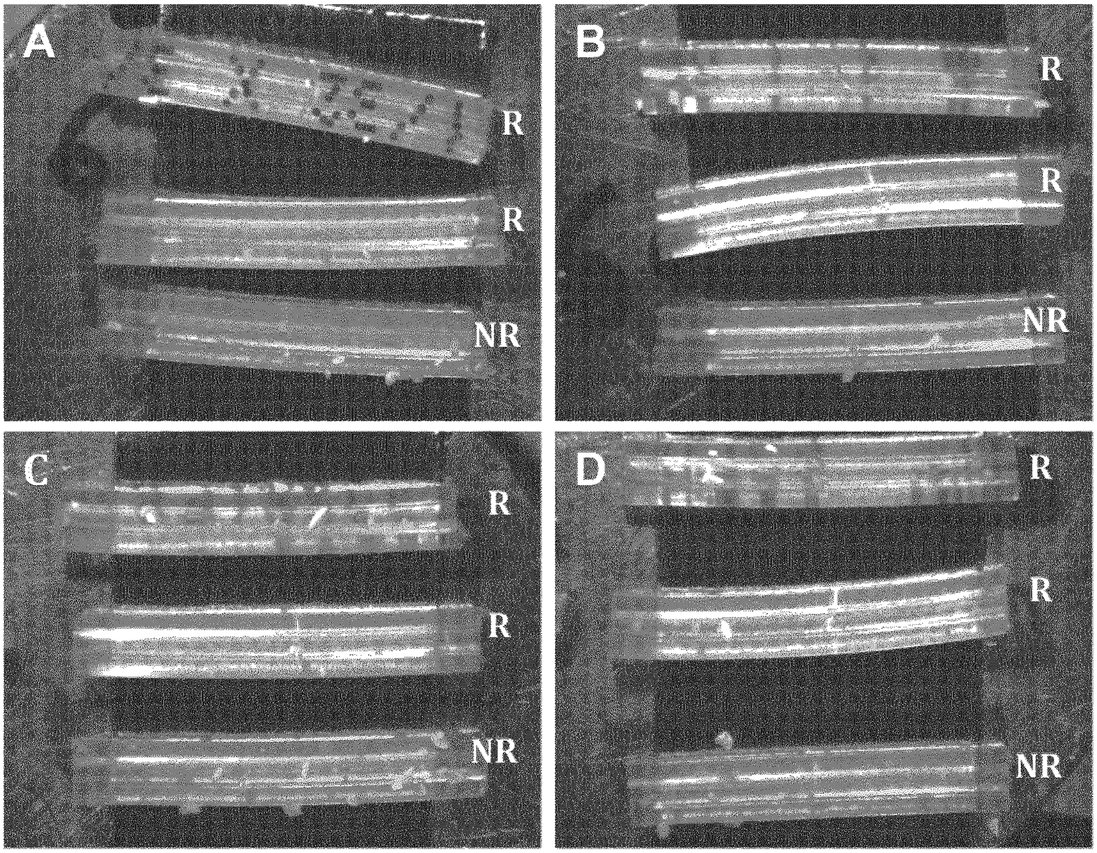
FIG. 3. Struvite crystals adhered in catheters in presence or absence of phytate at different concentrations of NH4+. (A) shows crystals (9 crystals) adhered using 9.28 g/L NH4+ with no phytate. (B) shows crystals (2 crystals) adhered using 9.28 g/L NH4+ with 1 ppm phytate. (C) shows crystals (12 crystals) adhered using 18.56 g/L NH4+ with no phytate. (D) shows crystals (5 crystals) adhered using 18.56 g/L NH4+ and 1 ppm phytate. R means washed catheter; NR means no washed catheter.

FIG. 3 shows struvite crystals adhered in catheters in presence or absence of phytate at different concentrations of $NH_4^+$: FIG. 3 A shows crystals (9 crystals) adhered using 9.28 g/L $NH_4^+$ with no phytate; FIG. 3 B shows crystals (2 crystals) adhered using 9.28 g/L $NH_4^+$ with 1 ppm phytate; FIG. 3 C shows crystals (12 crystals) adhered using 18.56 g/L $NH_4^+$ with no phytate and FIG. 3 D shows crystals (5 crystals) adhered using 18.56 g/L $NH_4^+$ and 1 ppm phytate (N means washed catheter; NR means no washed catheter). This experiment confirms the results shown in FIG. 1 and FIG. 2, i.e., that phytate has the capability to act as crystallization inhibitor of struvite in the presence of a catheter.

Example 3: Bacterial Adhesion in Catheters

The objective of this example was to observe if there is a significant decrease in the number of bacteria adhered to catheters in the presence of different concentrations of phytate.

Methodology

Artificial urine: The crystalline development was carried out in an artificial urine medium with the compositions shown in Table 5 and Table 6.

TABLE 5

Composition for artificial urine with calcium
Composition A (with Calcium)

| Substance | Concentration (g/L) |
|---|---|
| $Na_2SO_4•10H_2O$ | 6.23 |
| $MgSO_4•7H_2O$ | 1.46 |
| $NH_4Cl$ | 4.64 |
| KCl | 12.13 |
| $Ca^{2+}$ | 0.34 |

TABLE 6

Composition for artificial urine with oxalate, albumin, glucose and phytate
Composition B (with Oxalate, Albumin, Glucose and Phytate)

| Substance | Concentration (g/L) |
|---|---|
| $NaH_2PO_4•2H_2O$ | 2.41 |
| $Na_2HPO_4•12H_2O$ | 5.60 |
| NaCl | 13.05 |
| $Na_2C_2O_4$ | 0.08 |
| Bovine Serum Albumin | 2 |
| Glucose | 20 |
| Phytate | 1, 2 ppm |

The solutions were adjusted to pH 6.5, mixed in a 1:1 ratio and allowed to stand at 37° C. Once the experiment was carried out, 40 mL of the mixture of the two solutions in 50 mL Falcon tubes were added where a 1.5 cm catheter piece had previously been placed. The mixture stood 24 h at 37° C. Once past the established time, the catheters were removed.

Bacteria grow: *Pseudomonas aeruginosa* PAO1 was grown overnight in artificial urine without phytic acid to a final concentration of 108 colony forming units/ml and incubated at 37° C. without shaking.

Bacteria inoculation: 1.5 cm catheter sections were placed in sterile tubes containing 40 ml of artificial urine without or with phytic acid (1 ppm or 2 ppm). The tubes were inoculated with *Pseudomonas aeruginosa* PAO1 grown as mentioned above.

Bacteria adhesion determination: After 24 h, the catheter sections were removed with sterile tweezers, washed 3 times with sterile phosphate buffered saline (PBS) to remove unbound bacterial cells and placed in microcentrifuge tubes containing 1 ml of PBS. Bacteria bound to the catheter sections were collected by centrifugation at 13,000×g for 30 minutes and quantified by placing appropriate dilutions on Luria Bertani agar plates.

Results

Figure 4:
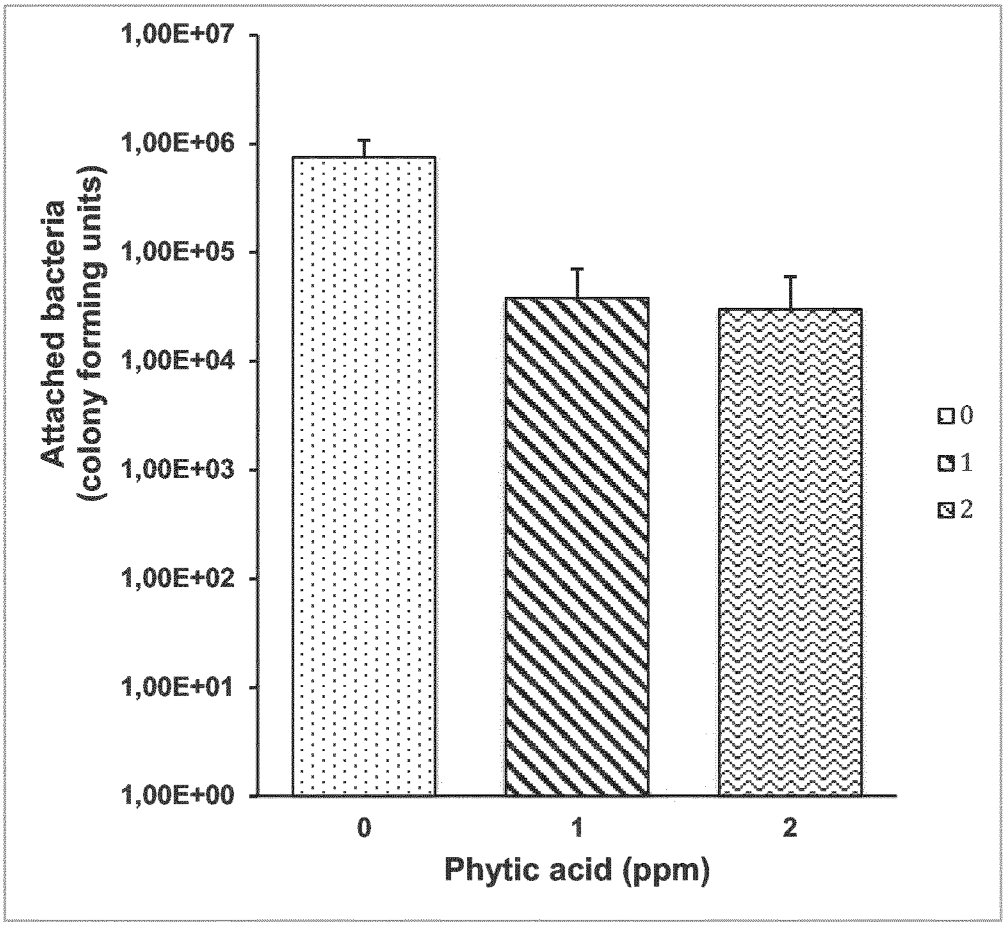
FIG. 4. Adhered bacteria in catheters in presence or absence of phytate expressed as average ±SE. 0: no phytate group; 1:1 ppm phytate; 2:2 ppm phytate. Significant differences are observed with a P-value <0.05 (T-student with independent samples) between the groups with and without phytate, being the adhered bacteria lower in the first one. No important difference is shown between the group with phytate at different concentrations (1 and 2 ppm).
Figure 5:
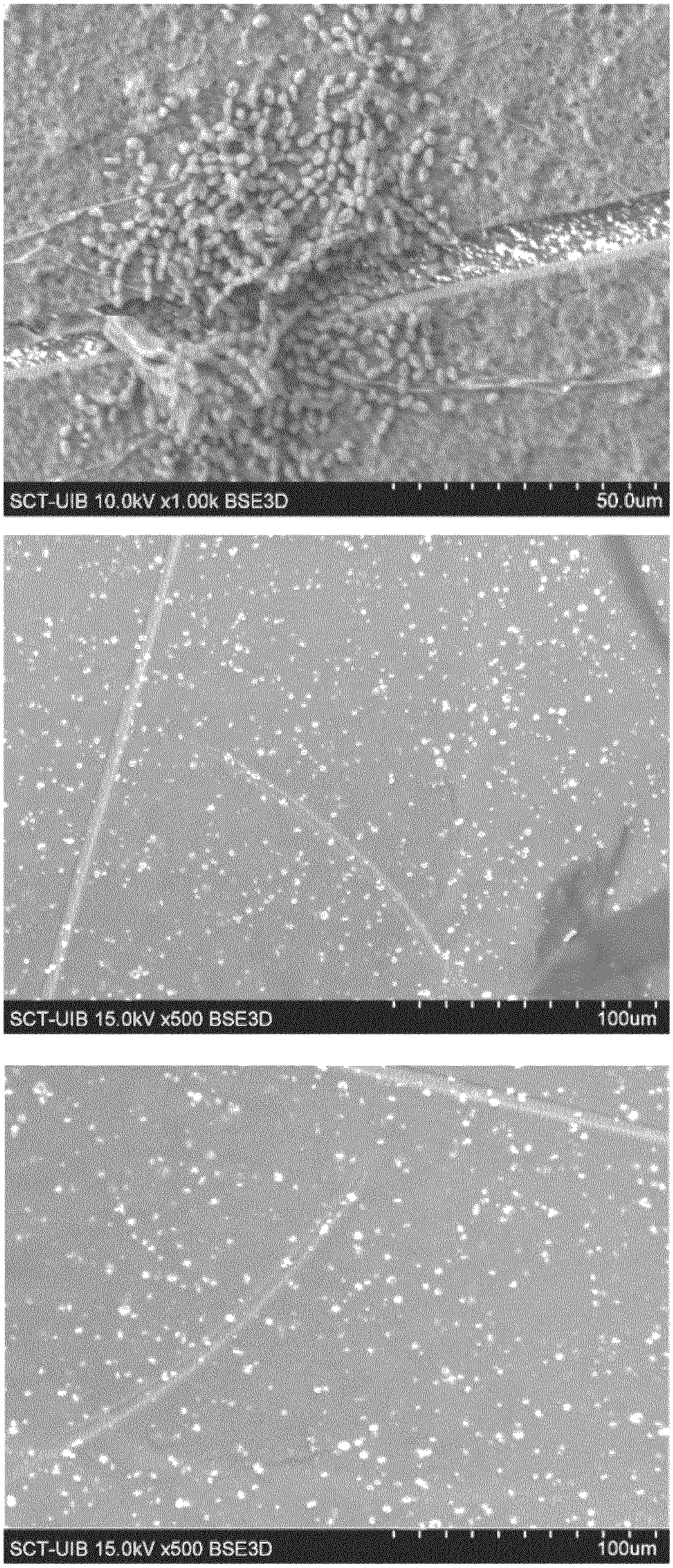
FIG. 5. Electron microscopy photography showing bacteria adhesion in catheter surface. (A) shows adhered bacteria with no phytate in the composition; (B) shows adhered bacteria with 1 ppm phytate in the composition; (C) shows adhered bacteria with 2 ppm phytate in the composition.

FIG. 4 shows a significative decrease in the number of adhered bacteria in the surface of incubated catheters with phytate 1 and 2 ppm. There are no important differences in bacteria adhesion between phytate concentrations (1 and 2 ppm); an explanation would be in both cases the adhesion inhibition is maximum. In FIG. 5 bacteria adhesion in catheter surface is illustrated; FIG. 5A shows adhered bacteria with no phytate in the composition; FIG. 5 B shows adhered bacteria with 1 ppm phytate in the composition and FIG. 5 C shows adhered bacteria with 2 ppm phytate in the composition. These results are consistent with the ones showed in FIG. 4: phytate causes a significative decrease in the number of adhered bacteria in catheters' surface.

Example 4: Formulation and Product Administration Guideline

The following table shows a commercial product composition:

TABLE 7

| Commercial product composition | |
|---|---|
| Ingredient | Quantity (mg) |
| Calcium magnesium phytate | 170 |
| L-methionine | 500 |
| Theobromine | 150 |
| Excipients | Hydroxypropylmethylcellulose - Stabilizer E464<br>Silicon dioxide - Anticacking agent E551<br>Maltodextrine - bulcking agent<br>Magnesium stearate - Stabilizer E470Eb<br>Titanium dioxide - dye |

Administration Guideline

There are two approximations depending on the patient situation i) Concerted implantation: the urinary tract device implantation is a solution for treating a urinary problem such as incontinence, urinary retention, or as a part of a surgery protocol. The patient will be prescribed the consumption of the product about 48/72 hours before the intervention, in order to create a hostile environment to microorganisms.

ii) Urgent implantation of a Doble J stent to manage urinary blockage caused by urinary stone: the urinary tract device implantation is a solution for treating said urgent urinary problem. The product will be supplied to the patient after the intervention, and if the medical conditions allow, a treatment guideline will be initialized.

The dosage is 3 tablets per day (1-1-1). In patients who by medical history or weakness, a urinary pH control is needed (i.e. with the need of reducing pH under 6.2), the guideline will be modified, probably with a dose increase. In contrast, if the urinary pH control shows the pH is too acid, a tablet will be removed.

Example 5: Prevention of Conditioning Film Generation

The objective of this experiment was to demonstrate the possibility to reduce or prevent the conditioning film formation. This organic film appears universally in all kinds of indwelling urological devices becoming a trigger for associated urinary infections. Thus, the conditioning film not only facilitates the formation and establishment of bacterial films, with the greater implicit resistance of these structures but also represents a point of crystalline heteronucleation resulting in the aforementioned virulence and resistance mechanisms on the part of bacteria.

Methodology

Artificial Urine and Continuous Flow System:

The experiment of conditioning film was carried out in an artificial urine medium with the compositions shown in Table 8 and Table 9. To avoid the precipitation of certain crystals as a result of the reaction of some solutes, part of two solutions were kept inert individually (Solution A and Solution B, FIG. 6), and were subsequently mixed within the continuous flow system, generating a new mixture with similar composition to the physiological urine. Solution A contains different salts (Table 8, Solution A with calcium) in concentrations that approximate the presence of cations and anions to the real ones ($Na_2SO_4.10H_2O$; $MgSO_4.7H_2O$; $NH_4Cl$; KCl; $CaCl_2$)). The use of a source of $NH_4^+$ ($NH_4Cl$) is of special interest, since it is a differential element in the urine of subjects with infection, asymptomatic bacteriuria or incipient bacteriuria, in addition to being a key element in the composition of magnesium ammonium phosphate crystals (struvite). The second solution (Solution B, mixed in a 1:1 ratio with Solution A in the T connection of the continuous flow system, FIG. 6) contains phosphates ($NaH_2PO_4.2H_2O$; $Na_2HPO_4.12H_2O$), sodium and chlorine, (in addition to NaCl) and mucin, as an organic molecule of a glycoprotein nature with a crucial role in the development of the organic film, or conditioning film, on medical devices implanted in urological patients.

TABLE 8

| Composition of artificial urine with calcium (Solution A + calcium) | |
|---|---|
| Ingredient | Concentration (g/L) |
| $Na_2SO_4•10H_2O$ | 6.23 |
| $MgSO_4•7H_2O$ | 1.46 |
| $NH_4Cl$ | 4.64 |
| KCl | 12.13 |
| [Ca] | 0.34 (8.5 mL $CaCl_2$ 1M) |

TABLE 9

| Composition of artificial urine with mucin (Solution B + Mucin) | |
|---|---|
| Ingredient | Concentration (g/L) |
| $NaH_2PO_4•2H_2O$ | 2.41 |
| $Na_2HPO_4•12H_2O$ | 5.60 |
| NaCl | 13.05 |
| Mucin | 0.2 |

Figure 6:
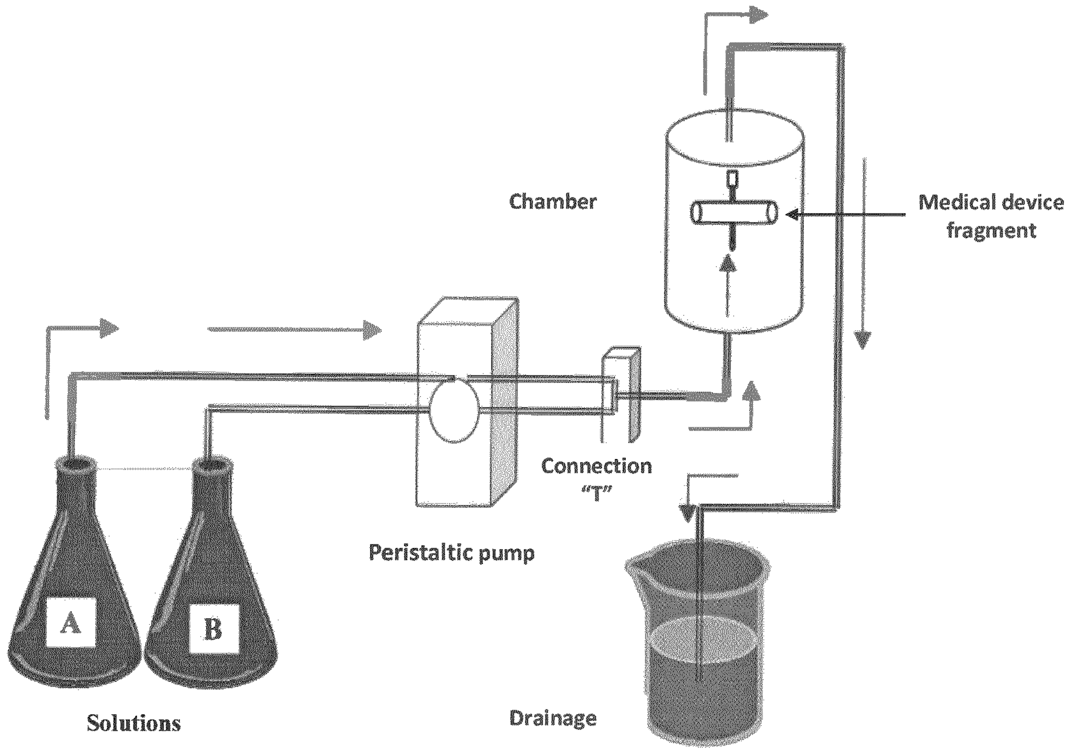
FIG. 6. Outline of the in vitro system used to simulate the urinary system. Solutions A and B are mixed in a 1:1 ratio in the T connection through a peristaltic pump generating artificial urine. Artificial urine is used to irrigate a medical device fragment used to emulate an indwelling urinary medical device. Urine flow is removed from the system through drainage at the end of the system simulating the micturition.

The generation of the glycoprotein film was emulated using the system shown in FIG. 6. Continuous irrigation of the medical device fragment with a flow (0.52 mL/min) of artificial urine obtained by the mixture of the Solutions A and B in the T connection facilitates the deposition of protein in the material surface. The medical device fragment (1.5 cm) of Tygon was located in a chamber (FIG. 6) and it was representative of the materials used in the manufacture of indwelling urological devices. The chamber (FIG. 6) mimics the different inner parts of the urinary system potentially indwelled by urological devices: renal pelvis, ureter, urinary bladder, or urethra. The flow of synthetic urine was kept constant for 48 hours, enough time (both in vitro and real) to observe the formation of the organic film.

Generation of the Experimental Conditions:

2 liters of each solution were prepared and adjusted to pH 6.5. The volume of Solution B was divided in the following 4 groups (each one containing 500 mL of the Solution B):

500 mL of Solution B (Control)

500 mL of Solution B+1 mL de N-acetylcysteine (NAC) 20 g/L (B NAC 40 mg/L)

500 mL of Solution B+2 mL phytate 1 g/L (B phytate 4 ppm)

500 mL of Solution B+1 mL de NAC 20 g/L+2 mL phytate 1 g/L (B NAC 40 mg/L phytate 4 ppm)

Solutions A and B were mixed 1:1 within each T connection (FIG. 6). In each of the compartments, a 1.5 cm piece of tube Tygon was attached to a support (needle), with continuously irrigation for 48 hours.

Quantification of the Protein Adhered to the Surface of the Material Fragment:

After 48 hours of running the experiment, the Tygon fragments were removed and left to dry until the next morning. The determination of mucin in each of the samples was carried out by the Lowry procedure: This procedure starts with the addition of homogenization buffer (TH) inside the test tubes containing dried fragments. The added volume should be a minimum of 1.5 mL, and sufficient to ensure that the fragment remains submerged. The next step is sonication (150 W) for 50 minutes to ensure that the protein layer is shed from the catheter surface. Before proceeding with the quantification of total protein in 96-well plates, a dilution bank should be performed. For this purpose, a BSA standard was used, processed in the same way as the samples. The calibration conditions and reactives are as shown below in Table 10A-B.

TABLE 10A

| Calibration and reaction conditions | | | | | | |
|---|---|---|---|---|---|---|
| Mucin [g/L] | 0 | 0.025 | 0.05 | 0.1 | 0.15 | 0.2 |
| Tube | 1 | 2 | 3 | 4 | 5 | 6 |
| Mucin (ml) | 0 | 0.025 | 0.05 | 0.1 | 0.15 | 0.2 |
| TH (ml) | 1 | 0.975 | 0.95 | 0.9 | 0.85 | 0.8 |

TABLE 10B

| | | |
|---|---|---|
| Standard curve/sample | 175 uL | |
| Lowry (Reactive 1) | 125 uL | 15 minutes, at room temperature, without light |
| Folin (Reactive 2) | 25 uL | 30 minutes, at room temperature, without light |

Results

Figure 7:
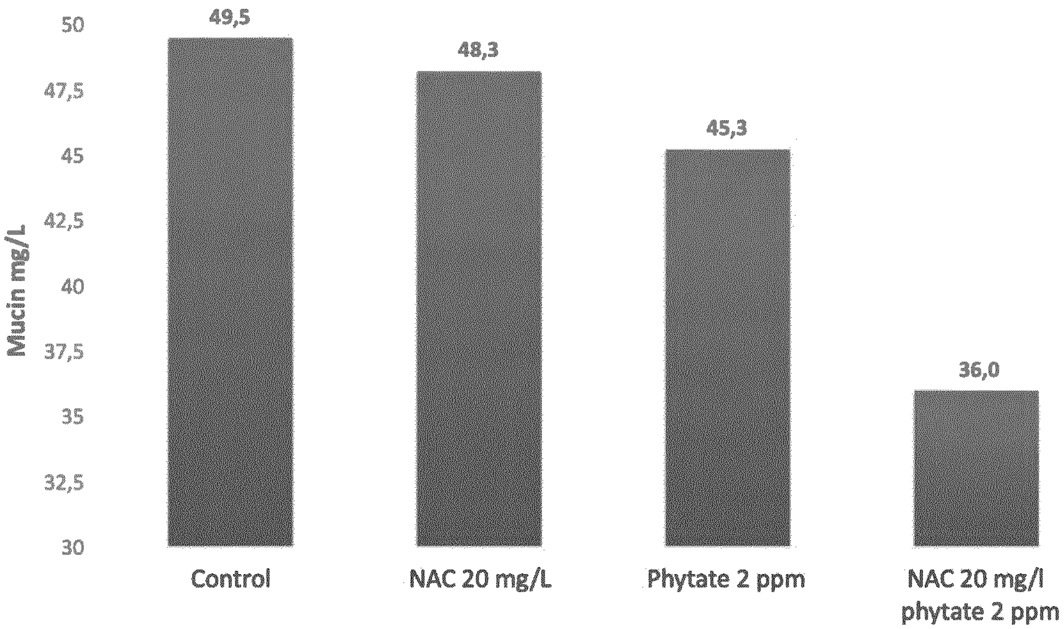
FIG. 7. Representation of the results obtained in the protein quantification after removal of mucin adhered to the medical device fragment by sonication. Each bar represents the different experimental conditions employed to demonstrate the reduction in the conditioning film formation. The control group was run allowing free protein deposition. The experiments were carried out using N-acetylcysteine (NAC) at 20 mg/L, phytate at 2 ppm, and the combination of both compounds.

The obtained results show that the accumulated protein (Table 11; FIG. 7) was lower in the experiments containing the combination of phytate and NAC (NAC 20 mg/L and phytate 2 ppm). The reduction in the amount of accumulated protein was close to 27%. In experiments where phytate (2 pp,) and NAC (20 mg/L) were tested individually, a reduction in the precipitation was observed but of less intensity (Table 11).

TABLE 11

Quantity of accumulated protein (Mucin)

| | Experiment 1 (mg/L) | Experiment 2 (mg/L) | Average (mg/L) |
|---|---|---|---|
| Control | 30.0 | 69.0 | 49.5 |
| NAC 20 mg/L | 30.0 | 66.5 | 48.3 |
| Phytate 2 ppm | 33.0 | 57.5 | 45.3 |
| NAC 20 mg/L phytate 2 ppm | 15.0 | 57.0 | 36.0 |

LIST OF REFERENCES www.devicare.com/en/devicare-obtiene-la-patente-en-europa-y-estados-unidos-de-su-tecnologia-sensorica/.

The invention claimed is:

1. A method of preventing or treating at least one clinical complication related to microorganisms' proliferation and/or encrustations in a subject in need thereof comprising orally administering to the subject a composition comprising phytic acid or a pharmaceutically acceptable salt thereof, wherein the microorganisms' proliferation and/or encrustations are caused by a urinary tract device implanted in the subject, and wherein the oral administration of the composition prevents or treats at least one clinical complication related to the microorganisms' proliferation and/or encrustations.

2. The method of claim 1, wherein the composition reduces the adhesion of the microorganisms to the surface of the implanted device and reduces or prevents encrustations on the surface of the device.

3. The method of claim 1, wherein the at least one complication is selected from the group consisting of bacteriuria, urinary tract infection, urethritis, pyelonephritis, sepsis, urinary tract device blockage, hydrophrenosis, renal failure, bladder distension, patient discomfort, catheter pain, polyuria, nocturia, dysuria, anuria, irritation, and any combination thereof.

4. The method of claim 1, wherein the urinary tract device is selected from the group consisting of: a urethral Foley catheter, a suprapubic Foley catheter, a ureteral JJ stent, an intermittent catheter or Robinson catheter, a coudé catheter, a hematuria catheter, a condom catheter, a bladder balloon, a prostatic stent, a single J stent, a three-luer Foley, a nephrostomy device, an urostomy device, and an ostomy device.

5. The method of claim 1, wherein the device is a catheter and the complication is a catheter-associated urinary tract infection.

6. The method of claim 1, wherein the encrustations comprise one or more crystals selected from the group consisting of ammonium phosphate crystals, calcium phosphate crystals, calcium oxalate crystals, uric acid crystals, and ammonium urate crystals.

7. The method of claim 6, wherein the ammonium phosphate crystals comprise struvite.

8. The method of claim 6, wherein the calcium phosphate crystals comprise brushite, hydroxyapatite, or a combination thereof.

9. The method of claim 1, wherein the microorganisms' proliferation is caused by one or more microorganisms selected from the group consisting of *Pseudomonas aeruginosa, Klebsiella pneumoniae/oxytoca, Morganella morganii, Proteus species, Providencia species, Staphylococcus aureus, Escherichia coli, Serratia marcescens, Enterococcus* sp., *Staphylococcus aureus, Enterobacter cloacae*, and coagulase-negative staphylococci.

10. The method of claim 1, wherein the composition is administered in combination with at least one urinary acidifier.

11. The method of claim 10, wherein the urinary acidifier is selected from the group consisting of a portion or an extract of the plant species Vaccinum, pharmaceutically acceptable ammonium salts, arginine and any of its pharmaceutically acceptable salts, cysteine and any of its pharmaceutically acceptable salts, methionine and any of its pharmaceutically acceptable salts, and any mixtures thereof.

12. The method of claim 10, wherein the urinary acidifier is methionine.

13. The method of claim 1, wherein the phytic acid or a pharmaceutically acceptable salt thereof is derived from a portion of a plant species rich in phytic acid or its salts, or from a plant extract of said plant species.

14. The method of claim 1, wherein the pharmaceutically acceptable salt of phytic acid is selected from the group consisting of sodium phytate, potassium phytate, calcium phytate, magnesium phytate, zinc phytate, calcium-magnesium phytate, and any combination thereof.

15. The method of claim 1, wherein the composition is administered in combination with theobromine.

16. The method of claim 15, wherein the combination further comprises a mucolytic agent.

17. The method of claim 16, wherein the mucolytic agent is N-acetylcysteine.

18. The method of claim 17, wherein the combination further comprises methionine.

19. A method of preventing of reducing struvite encrustation on a urinary tract device implanted in a subject in need thereof comprising orally administering to the subject an effective amount of a composition comprising phytic acid or a pharmaceutically acceptable salt thereof, wherein the composition prevents or reduces struvite encrustations on the urinary tract device.

20. A method of preventing or treating at least one clinical complication related to microorganisms' proliferation and/or encrustations in a subject in need thereof comprising administering to the subject a composition comprising phytic acid or a pharmaceutically acceptable salt thereof in combination with theobromine, wherein the microorganisms' proliferation and/or encrustations are caused by a urinary tract device implanted in the subject, wherein the administration of the composition prevents or treats at least one clinical complication related to the microorganisms' proliferation and/or encrustations.

* * * * *